US011832860B2

(12) United States Patent
DeGeorge, Jr. et al.

(10) Patent No.: US 11,832,860 B2
(45) Date of Patent: Dec. 5, 2023

(54) BONE FIXATION SYSTEM FOR PROMOTING THE UNION OF A BONE FRACTURE AND FUSION OF BONES ACROSS A JOINT SPACE AND RELATED METHODS THEREOF

(71) Applicant: University of Virginia Patent Foundation, Charlottesville, VA (US)

(72) Inventors: Brent R. DeGeorge, Jr., Charlottesville, VA (US); Patrick S. Cottler, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 16/973,404

(22) PCT Filed: Jun. 21, 2019

(86) PCT No.: PCT/US2019/038532
§ 371 (c)(1),
(2) Date: Dec. 8, 2020

(87) PCT Pub. No.: WO2019/246556
PCT Pub. Date: Dec. 26, 2019

(65) Prior Publication Data
US 2021/0244453 A1     Aug. 12, 2021

Related U.S. Application Data

(60) Provisional application No. 62/864,434, filed on Jun. 20, 2019, provisional application No. 62/688,566, filed on Jun. 22, 2018.

(51) Int. Cl.
*A61B 17/86* (2006.01)
*A61B 17/88* (2006.01)
(Continued)

(52) U.S. Cl.
CPC .......... *A61B 17/864* (2013.01); *A61B 17/863* (2013.01); *A61B 17/8816* (2013.01);
(Continued)

(58) Field of Classification Search
CPC . A61B 17/863; A61B 17/864; A61B 17/8816; A61B 17/7098; A61B 17/8625;
(Continued)

(56) References Cited

U.S. PATENT DOCUMENTS

| 5,743,912 A | 4/1998 | Lahille et al. |
| 7,717,947 B1 * | 5/2010 | Wilberg ............... A61B 17/864 606/304 |

(Continued)

FOREIGN PATENT DOCUMENTS

WO    WO 02/098307    12/2002

OTHER PUBLICATIONS

Adams, JE, et al., "Acute Scaphoid Fractures", Hand Clinics 2010 (this article originally appeared in Orthopedic Clinics of North America 2007;38(2):229-35), pp. 97-103, vol. 26, No. 1.
(Continued)

*Primary Examiner* — Marcela I. Shirsat
(74) *Attorney, Agent, or Firm* — Robert J. Decker

(57) ABSTRACT

A method and system for promoting the union of a bone fracture and/or fusion of bones across a joint space at a target region of a subject which may be accomplished by: inserting a surgical implant device at the target region; providing a guide member in the surgical implant device bore; sealing the surgical implant device bore distal opening and/or the surgical implant device bore proximal opening with the guide member; and positioning the guide member relative to the surgical implant device to provide for the guide member to be partially absent from the surgical implant device bore to allow the biomaterial and/or biologically active agents to
(Continued)

(51) Int. Cl.
*A61B 17/56* (2006.01)
*A61B 17/04* (2006.01)
*A61B 17/70* (2006.01)

(52) U.S. Cl.
CPC ...... *A61B 17/8897* (2013.01); *A61B 17/7098* (2013.01); *A61B 17/8605* (2013.01); *A61B 17/8645* (2013.01); *A61B 17/8805* (2013.01); *A61B 17/8819* (2013.01); *A61B 17/8833* (2013.01); *A61B 2017/0445* (2013.01); *A61B 2017/561* (2013.01)

(58) Field of Classification Search
CPC ............ A61B 17/8819; A61B 17/7032; A61B 17/8822; A61B 17/68; A61B 17/8605; A61B 17/3472; A61B 17/8805; A61B 17/86; A61B 17/7097; A61B 17/8833; A61B 17/72; A61B 17/8645; A61B 17/8802; A61B 17/8897; A61B 17/8061; A61B 17/846; A61B 2017/561; A61B 2017/564; A61B 2017/00557; A61B 2017/0648; A61B 2017/0445
USPC ... 606/300, 301, 304, 316, 321, 329, 92, 93, 606/95
See application file for complete search history.

(56) References Cited

U.S. PATENT DOCUMENTS

| | | | |
|---|---|---|---|
| 8,216,243 | B2 | 7/2012 | Yevmenenko et al. |
| 8,979,911 | B2 | 3/2015 | Martineau et al. |
| 9,265,540 | B2 | 2/2016 | Kirschman |
| 9,603,644 | B2 | 3/2017 | Sweeney |
| 2007/0233123 | A1 | 10/2007 | Ahmad et al. |
| 2010/0030135 | A1* | 2/2010 | Mitchell ............... A61M 31/00 606/305 |
| 2011/0004256 | A1* | 1/2011 | Biedermann ......... A61F 2/4614 606/86 R |
| 2014/0058461 | A1 | 2/2014 | Black |
| 2017/0258503 | A1 | 9/2017 | Aebi et al. |

OTHER PUBLICATIONS

Arcam AB, "Arcam system: Arcam-Ti6Al4V-Titanium-Alloy", 4 pages (http://www.arcam.com/wp-content/uploads/Arcam-Ti6Al4V-Titanium-Alloy.pdf).

Beutel, Bryan G., et al., "Mechanical Evaluation of Four Internal Fixation Constructs for Scaphoid Fractures", Hand (Hand Surgery), Mar. 2016 (published online Jan. 13, 2016), pp. 72-77, vol. 11, No. 1.

Bond, Charles D., et al., "Percutaneous Cannulated Screw Fixation of Acute Scaphoid Fractures", Techniques in Hand and Upper Extremity Surgery, Jun. 2000, pp. 81-87, vol. 4, No. 2.

Boyd, Anne S., et al., "Splints and Casts: Indications and Methods", American Family Physician, Sep. 1, 2009, pp. 491-499, vol. 80, No. 5.

Brogan, David M., et al., "Outcomes of open reduction and internal fixation of acute proximal pole scaphoid fractures", Hand, Jun. 2015 (published online: Oct. 15, 2014), pp. 227-232, vol. 10, No. 2, American Association for Hand Surgery.

Buijze, Geert A., et al., "Management of Scaphoid Nonunion", Journal of Hand Surgery, May 2012, pp. 1095-1100, vol. 37A, No. 5.

Compson, J.P., et al., "Imaging the Position of a Screw Within the Scaphoid: A clinical, anatomical and radiological study", The Journal of Hand Surgery, Dec. 1993, pp. 716-724, vol. 18B, No. 6.

David Schafer & Associates, "Strength Requirements and Characteristics of Pipe and Well Screen for Deep Water Well Applications", Los Alamos National Laboratory, Apr. 2002, 17 pages.

Davis, Erika N., et al., "A Cost/Utility Analysis of Open Reduction and Internal Fixation versus Cast Immobilization for Acute Nondisplaced Mid-Waist Scaphoid Fractures", Plastic and Reconstructive Surgery, Apr. 1, 2006, pp. 1223-1235, vol. 117, No. 4.

Degeorge Jr., Brent R., et al., "The Impact of Conflict of Interest in Abdominal Wall Reconstruction With Acellular Dermal Matrix", Annals of Plastic Surgery, Feb. 2015, pp. 242-247, vol. 74, No. 2.

Degeorge, Jr., Brent R., et al., "The Biophysical Characteristics of Human Composite Flexor Tendon Allograft for Upper Extremity Reconstruction", Annals of Plastic Surgery, Jun. 2014, pp. S184-S190, vol. 72 (S2), No. 6.

Degeorge, Jr., Brent R., et al., "Advanced Imaging Techniques for Investigation of Acellular Dermal Matrix Biointegration", Plastic and Reconstructive Surgery, Feb. 2017, pp. 395-405, vol. 139, No. 2.

Doornberg, Job N., et al., "Nonoperative Treatment for Acute Scaphoid Fractures: A Systematic Review and Meta-Analysis of Randomized Controlled Trials", The Journal of TRAUMA® Injury, Infection, and Critical Care, Oct. 2011, pp. 1073-1081, vol. 71, No. 4.

Elhassan, Bassem T., et al., "Scaphoid Fracture in Children", Hand Clinics, Feb. 2006, pp. 31-41, vol. 22, No. 1.

Fowler, John R., et al., "Scaphoid Fractures", Clinics in Sports Medicine, Jan. 2015, pp. 37-50, vol. 34, No. 1.

Garcia, P., et al., "Rodent Animal Models of Delayed Bone Healing and Non-Union Formation: A Comprehensive Review", European Cells and Materials, 2013, pp. 1-14, vol. 26.

Gibbs, David M. R., et al., "A review of hydrogel use in fracture healing and bone regeneration", Journal of Tissue Engineering and Regenerative Medicine, Mar. 2016 (published online Dec. 10, 2014), pp. 187-198, vol. 10, No. 13.

Giddins, Grey, "The Nonoperative Management of Hand Fractures in United Kingdom", Hand Clinic, Aug. 2017, pp. 473-487, vol. 33, No. 3.

Griffin, Donald R., et al., "Accelerated wound healing by injectable microporous gel scaffolds assembled from annealed building blocks", Nature Materials, Jul. 2015, pp. 737-744, vol. 14, No. 7.

Hak, David J., et al., "Recombinant Human BMP-7 Effectively Prevents Non-Union in Both Young and Old Rats", Journal of Orthopaedic Research, Jan. 2006 (published online Oct. 7, 2005), vol. 24, No. 1, pp. 11-20.

Kawamura, Kenji, et al., "Treatment of Scaphoid Fractures and Nonunions", The Journal of Hand Surgery, 2008, pp. 988-997, vol. 33, No. 6.

McCallister, Wren V., et al., "Central Placement of the Screw in Simulated Fractures of the Scaphoid Waist", The Journal of Bone and Joint Surgery, Jan. 2003, pp. 72-77, vol. 85-A, No. 1.

Merrell, Gregory A., et al., "Treatment of Scaphoid Nonunions: Quantitative Meta-Analysis of the Literature", The Journal of Hand Surgery, Jul. 2002, pp. 685-691, vol. 27, No. 4.

Munk, Bo, et al., "Bone grafting the scaphoid nonunionA systematic review of 147 publications including 5 246 cases of scaphoid nonunion", Acta Orthopaedica Scandinavica, 2004, pp. 618-629, vol. 75, No. 5.

Nih, Lina R., et al., "Injection of Microporous Annealing Particle (MAP) Hydrogels in the Stroke Cavity Reduces Gliosis and Inflammation and Promotes NPC Migration to the Lesion", Advanced Materials, Aug. 25, 2017, 1606471 (8 pages), vol. 29, No. 32.

Nwachukwu, Benedict U., et al., "The Quality of Cost-Utility Analyses in Orthopedic Trauma", Orthopedics, Aug. 2015, pp. e673-e680, vol. 38, No. 8.

Papp, Steven, "Carpal Bone Fractures", Hand Clinics, Feb. 2010 (originally appeared in Orthopedic Clinics of North America 2007;38(2):251-60), pp. 119-127, vol. 26, No. 1.

(56) References Cited

OTHER PUBLICATIONS

Pensy, Raymond A., et al., "Biomechanical Comparison of Two Headless Compression Screws for Scaphoid Fixation", Journal of Surgical Orthopaedic Advances, 2009, pp. 182-188, vol. 18, No. 4.

Pichler, Wolfgang, et al., "Computer-assisted 3-Dimensional Anthropometry of the Scaphoid", Orthopedics, Feb. 2010, pp. 85-88, vol. 33, No. 2.

Pinder, Richard M., et al., "Treatment of Scaphoid Nonunion: A Systematic Review of the Existing Evidence", Journal of Hand Surgery (American Volume), Sep. 2015, pp. 1797-1805.e3, vol. 40, No. 9.

Renkin, Eugene M., "Filtration, Diffusion, and Molecular Sieving Through Porous Cellulose Membranes", The Journal of General Physiology, 1954, pp. 225-243, vol. 38, No. 2.

Rizzo, Marco, et al., "Treatment of Acute Scaphoid Fractures in the Athlete", Current Sports Medicine Reports, Sep. 2006, pp. 242-248, vol. 5, No. 5.

Schuind, F., et al., "Force and Pressure Transmission Through the Normal Wrist. A Theoretical Two-Simensional Study in the Posteroanterior Plane", Journal of Biomechanics, May 1995, vol. 28, No. 5, pp. 587-601.

Sendher, Rosie, et al., "The Scaphoid", Orthopedic Clinics of North America, Jan. 2013, pp. 107-120, vol. 44, No. 1.

Shah, Chirag, et al., "Scapholunate advanced collapse (SLAC) and scaphoid nonunion advanced collapse (SNAC) wrist arthritis", Current Reviews in Musculoskeletal Medicine, Mar. 2013, pp. 9-17, vol. 6, No. 1.

Sideris, Elias, et al., "Particle Hydrogels Based on Hyaluronic Acid Building Blocks", ACS Biomaterials Science & Engineering, Sep. 7, 2016, pp. 2034-2041, vol. 2, No. 11.

Steinmann, Scott P., et al., "Scaphoid fractures and nonunions: diagnosis and treatment", Journal of Orthopaedic Science, Jul. 2006, pp. 424-431, vol. 11, No. 4.

Streli, Von R., "Perkutane Verschraubung des Handkahnbeines mit Bohrdrahtkompressionsschraube (Eine neue Methode)", [Percutaneous screwing of the navicular bone of the hand with a compression drill screw (a new method)], Zentralblatt fur Chirurgie. 1970, pp. 1060-1078, vol. 95, No. 36—w/ Google translation.

Ten Berg, Paul W., et al., "Classifications of Acute Scaphoid Fractures: A Systematic Literature Review", Journal of Wrist Surgery, May 2016 (published online Jan. 15, 2016), pp. 152-159, vol. 5, No. 2.

The Royal Alexandria Hospital for Children, "A device for the deliveiy of a drug to a fractured bone", Australian Provisional Specification PR 5537, Jun. 7, 2011, 16 pages, Priority document for PCT/AU02/00482.

Tholpady, Sunil S., et al., "The Effect of Local Rho-Kinase Inhibition on Murine Wound Healing", Annals of Plastic Surgery, Jun. 2014, pp. S213-S219, vol. 72, No. 6, Supp. 2.

Tobin, Eric J., "Recent coating developments for combination devices in orthopedic and dental applications: A literature review", Advanced Drug Delivery Reviews, Mar. 2017 (available online Feb. 1, 2017), pp. 88-100, vol. 112.

Trimed Inc., "Headless 1.7, 2.3, 3.0 & 3.5mm Screws", (2003-2022), 2 pages, found at https://trimedortho.com/portfolio-items/1-7-2-3-3-0-3-5mm-screws.

Wolf, Jennifer Moriatis, et al., "The incidence of scaphoid fracture in a military population", Injury, International Journal of the Care of the Injured, Dec. 2009, pp. 1316-1319, vol. 40, No. 12.

Zamanian, Kamran, et al., "U.S. Orthopedic Trauma Device Market To Exceed 8 Billion By 2020", Med Device Online, Jul. 5, 2014, 2 pages, found at https://www.meddeviceonline.com/doc/u-s-orthopedic-trauma-device-market-to-exceed-eight-billion-dollars-0001.

Zura, Robert, et al., "Epidemiology of Fracture Nonunion in 18 Human Bones", JAMA Surgery, Nov. 2016, 12 pages, e162775, vol. 151, No. 11.

Swedish Standards Institution, "Conical fittings with a 6% (Luer) taper for syringes, needles, and certain other medical equipment—Lock fittings", English version, European Standard, Nov. 1996, 20 pages, SS-EN 1707.

* cited by examiner

BONE FIXATION SYSTEM FOR PROMOTING THE UNION OF A BONE FRACTURE AND FUSION OF BONES ACROSS A JOINT SPACE AND RELATED METHODS THEREOF

RELATED APPLICATIONS

The present application is a national stage filing of International Application No. PCT/US2019/038532, filed Jun. 21, 2019, which claims benefit of priority under 35 U.S.C § 119 (e) from U.S. Provisional Application Ser. No. 62/688,566, filed Jun. 22, 2018, entitled "Fenestrated-Shaft Cannulated Screw as a Percutaneous Delivery Vehicle for Microporous Annealed Particle Scaffold for Fractures of the Bone" and U.S. Provisional Application Ser. No. 62/864,434, filed Jun. 20, 2019, entitled "Bone Fixation System for Promoting the Union of a Bone Fracture and Fusion of Bones Across a Joint Space and Related Methods Thereof"; the disclosures of which are hereby incorporated by reference herein in their entirety.

FIELD OF INVENTION

The present disclosure relates generally to medical devices, and more particularly a system and method for bone fixation and joint fusion.

BACKGROUND

The scaphoid is the most frequently fractured carpal bone, representing fifty to eighty percent of fractures of the carpus and three percent of fractures of the wrist. The mechanism of injury in fractures of the scaphoid is commonly a consequence of a fall onto an outstretched hand or a direct blow to the wrist, most typically affecting young men in their most active and productive years. Scaphoid fractures typically occur in young, healthy males at the peak of their productivity, and left inadequately treated will ultimately progress to non-union and a "predictable" pattern of wrist arthritis and carpal collapse. Non-operative treatment of these fractures requires prolonged cast immobilization, which can lead to wrist 30 stiffness, loss of grip strength, muscle atrophy, and protracted loss of productivity. To prevent these devastating sequelae, percutaneous techniques for scaphoid fixation have been described and popularized, however these techniques are technically demanding as optimal position of the compression screw is required to achieve bony union. Currently, a major obstacle in the field is that despite best clinical practice between four to twenty percent of these fractures go on to develop non-union with resultant pain, loss of motion, and often the requirement for additional operative procedures.

Therefore, there is a long felt need for a system to provide easier and improved access while applying an implant device to the target region or site of the subject, while reducing the trauma imposed on the subject. Therefore, there is a long felt need for a system to achieve greater flexibility and effectiveness in applying biomaterial and/or biologically active agents to a target region or site of a subject through the application of the implant device.

SUMMARY OF ASPECTS OF EMBODIMENTS OF THE INVENTION

An aspect of an embodiment provides, among other things, a percutaneous implant device that may be utilized for fixation of fractures of the scaphoid or other bones or fusion of bones across joint spaces. An aspect of an embodiment provides, among other things, a percutaneous implant device that provides a delivery vehicle for biomaterials or the like with osteogenic potential to improve bony union. An aspect of an embodiment provides, among other things, a percutaneous implant device that achieves an active substance delivery of biomaterials or the like through the apertures (e.g. fenestrations) of the implant device directly into the fracture site or bone joint. Furthermore, an aspect of an embodiment provides, among other things, a percutaneous implant device that apply, for example but not limited thereto, a class of injectable biomaterial utilizing micro-gel building blocks to assemble a microporous annealed particle (MAP) scaffold. The MAP scaffold has been engineered with a "plug and play" nature to recapitulate the physiologic niche of bone in terms of extracellular macromolecules (hyaluronic acid) and signals (bone morphogenetic protein-2 (BMP-2) to enable local tissue ingrowth into the scaffold. An aspect of an embodiment provides, among other things, a percutaneous implant device wherein the MAP scaffold is specifically engineered to be delivered through the fenestrated-implant device to augment bone healing and joint fusion.

An aspect of an embodiment provides, among other things, a percutaneous implant device that has the potential to revolutionize the management of scaphoid fractures and allow for the management of more complex scaphoid fracture patterns through a percutaneous approach; thus mitigating the potential pitfalls of an open operative approach to the scaphoid or other bones and joints. Furthermore, this approach could be applied to all orthopedic challenges that suffer high rates of non-union and are managed with a screw or rod technique, including hand and wrist procedures, foot and ankle procedures, and spine reconstruction, etc.

An aspect of an embodiment of the present invention provides, among other things, a method and system for promoting the union of a bone fracture and/or fusion of bones across a joint space at a target region of a subject which may be accomplished by: inserting a surgical implant device at the target region; providing a guide member in the surgical implant device bore; sealing the surgical implant device bore distal opening and/or the surgical implant device bore proximal opening with the guide member; and positioning the guide member relative to the surgical implant device to provide for the guide member to be partially absent from the surgical implant device bore thereby defining a guide member-absent bore area in the surgical implant device bore to allow the biomaterial and/or biologically active agents to extrude or diffuse from at least one of the apertures located in the guide member-absent bore area to the target region of the subject. In an embodiment the surgical implant device may be sealed with a cap or the like instead of the guide member. In an embodiment, the surgical implant device may be sealed with a cap or the like after the guide member has been removed from one or both ends of the bore of the surgical implant device.

An aspect of an embodiment of the present invention provides, among other things, a method and system for promoting the union of a bone fracture and/or fusion of bones across a joint space at a target region of a subject which may be accomplished by: inserting a surgical implant device at the target region; providing a guide member in the surgical implant device bore; sealing the surgical implant device bore distal opening and/or the surgical implant device bore proximal opening with the guide member; and positioning the guide member relative to the surgical implant device to provide for the guide member to be partially absent from the surgical implant device bore to allow the biomaterial and/or biologically active agents to extrude or diffuse from the activated apertures to the target region of the subject.

An aspect of an embodiment of the present invention provides, among other things, a bone fixation system for promoting the union of a bone fracture and fusion of bones across a joint space at a target region of a subject. The system may comprise: a surgical implant device, comprising a surgical implant device proximal end, a surgical implant device distal end and a surgical implant device longitudinal member there between and a surgical implant device bore running longitudinally there through the surgical implant device longitudinal member along its longitudinal axis, the surgical implant device bore comprising a surgical implant device bore proximal opening on the longitudinal axis and a surgical implant device bore distal opening on the longitudinal axis; a plurality of apertures disposed on the surgical implant device longitudinal member providing a fluidic passage between an outer surface of the surgical implant device longitudinal member and the surgical implant device bore; the surgical implant device bore proximal opening being configured to provide a fluidic passage for biomaterial material and/or biologically active agents therein; the surgical implant device bore, the surgical implant device bore distal opening, and the surgical implant device bore proximal opening being configured to be inserted over a guide member and a to have the guide member advanced or retracted therein the surgical device; and the surgical implant device bore distal opening being configured to be sealed by the guide member disposed in the surgical implant device bore distal opening while the guide member is partially absent from the surgical implant device bore thereby defining a guide member-absent bore area in the surgical implant device bore to allow the biomaterial and/or biologically active agents to extrude or diffuse from at least one of the apertures located in the guide member-absent bore area to the target region of the subject.

An aspect of an embodiment of the present invention provides, among other things, a surgical kit comprising: a guide member; and a bone fixation system for promoting the union of a bone fracture and fusion of bones across a joint space at a target region of a subject. The system may comprise: a surgical implant device, comprising a surgical implant device proximal end, a surgical implant device distal end and a surgical implant device longitudinal member there between and a surgical implant device bore running longitudinally there through the surgical implant device longitudinal member along its longitudinal axis, the surgical implant device bore comprising a surgical implant device bore proximal opening on the longitudinal axis and a surgical implant device bore distal opening on the longitudinal axis; a plurality of apertures disposed on the surgical implant device longitudinal member providing a fluidic passage between an outer surface of the surgical implant device longitudinal member and the surgical implant device bore; the surgical implant device bore proximal opening being configured to provide a fluidic passage for biomaterial material and/or biologically active agents therein; the surgical implant device bore, the surgical implant device bore distal opening, and the surgical implant device bore proximal opening being configured to be inserted over the guide member and a to have the guide member advanced or retracted therein the surgical device; and the surgical implant device bore distal opening being configured to be sealed by the guide member disposed in the surgical implant device bore distal opening while the guide member is partially absent from the surgical implant device bore thereby defining a guide member-absent bore area in the surgical implant device bore to allow the biomaterial and/or biologically active agents_to extrude or diffuse from at least one of the apertures located in the guide member-absent bore area to the target region of the subject.

An aspect of an embodiment of the present invention provides, among other things, a method for promoting the union of a bone fracture and/or fusion of bones across a joint space at a target region of a subject. The method may comprise inserting a surgical implant device at the target region. The surgical implant device may comprise: a surgical implant device proximal end, a surgical implant device distal end and a surgical implant device longitudinal member there between and a surgical implant device bore running longitudinally there through the surgical implant device longitudinal member along its longitudinal axis, the surgical implant device bore comprising a surgical implant device bore proximal opening on the longitudinal axis and a surgical implant device bore distal opening on the longitudinal axis; a plurality of apertures disposed on the surgical implant device longitudinal member providing a fluidic passage between an outer surface of the surgical implant device longitudinal member and the surgical implant device bore; and the surgical implant device bore opening being configured to provide a fluidic passage for biomaterial material and/or biologically active agents_therein. Moreover, the method may also comprise: providing a guide member in the surgical implant device bore; sealing the surgical implant device bore distal opening or the surgical implant device bore proximal opening with the guide member; and positioning the guide member relative to the surgical implant device to provide for the guide member to be partially absent from the surgical implant device bore thereby defining a guide member-absent bore area in the surgical implant device bore to allow the biomaterial and/or biologically active agents to extrude or diffuse from at least one of the apertures located in the guide member-absent bore area to the target region of the subject.

An aspect of an embodiment of the system (or components and subcomponents of the system) may be used multiple times in a single procedure and stored in a sterile container or environment until the specified time and place of use. Alternatively, the apparatus may be single use or disposable.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/operator/customer/client/server or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

The invention itself, together with further objects and attendant advantages, will best be understood by reference to the following detailed description, taken in conjunction with the accompanying drawings.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings.

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF ASPECTS OF EXEMPLARY EMBODIMENTS

Figure 1:
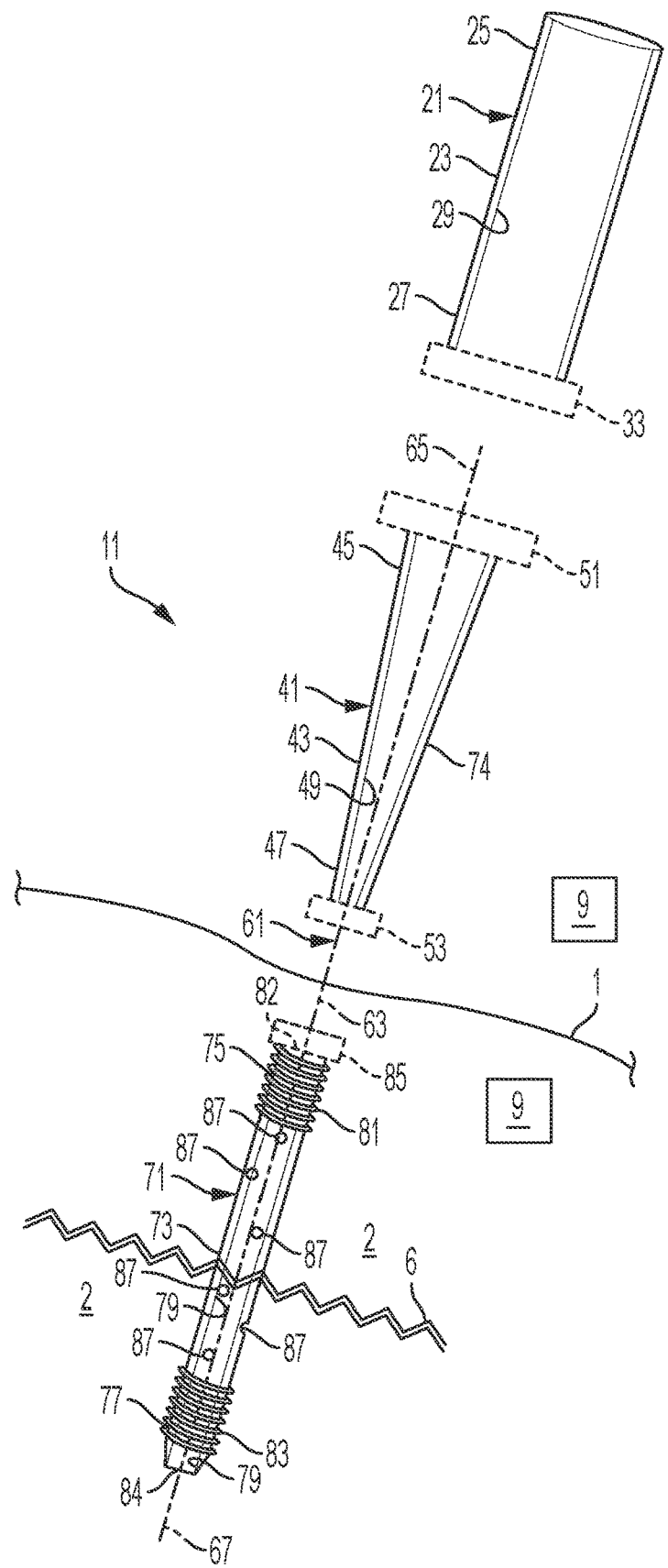
FIG. 1 schematically illustrates an embodiment an embodiment of the surgical implant device (having a tapered distal end) and an interface device that is positioned over a guide member, and a biomaterial and/or biologically active agents delivery device.

FIG. 1 schematically illustrates an embodiment an embodiment of a system 11 associated with a surgical implant device (having a tapered distal end) 71 and an interface device 41 that is positioned over a guide member 61, and a biomaterial and/or biologically active agents delivery device 21.

Figure 2:
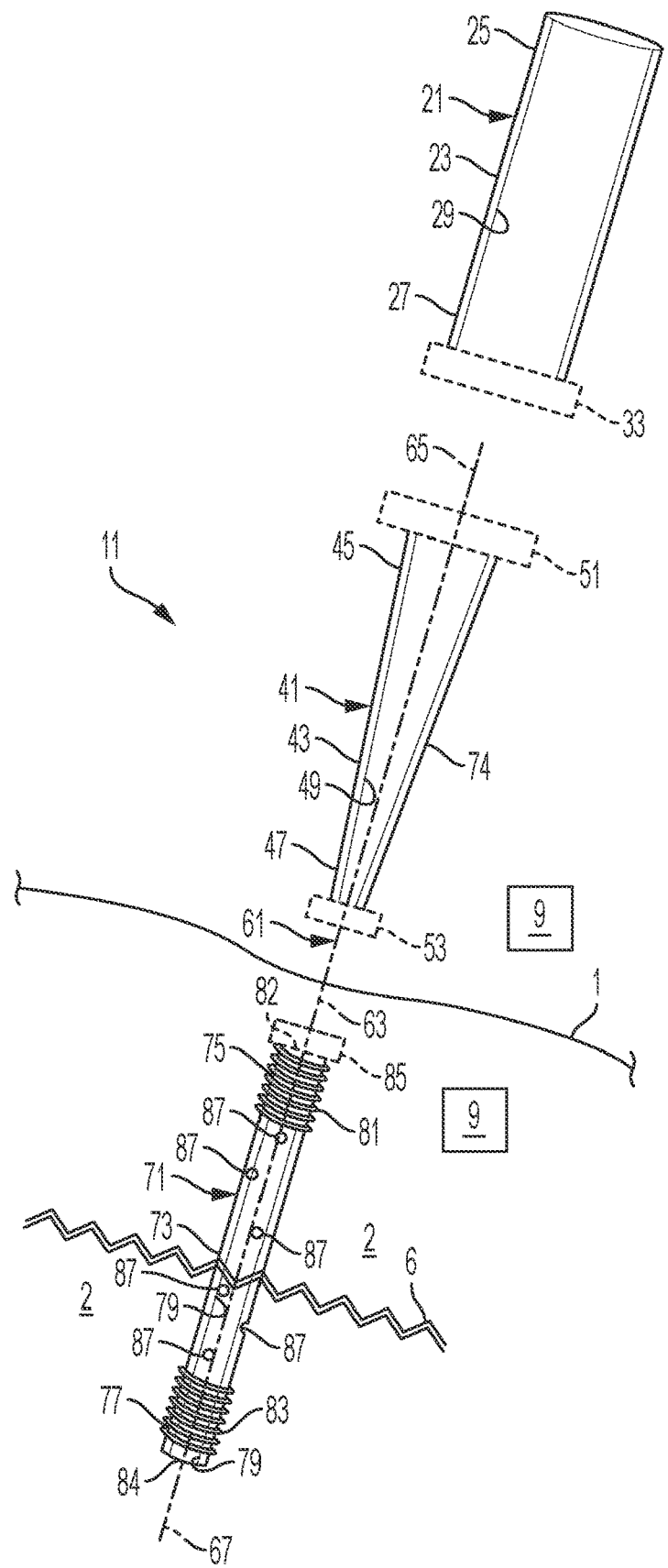
FIG. 2 schematically illustrates an embodiment of an embodiment of the surgical implant device (having a generally flat distal end) and an interface device that is positioned over a guide member, and a biomaterial and/or biologically active agents delivery device.

FIG. 2 schematically illustrates an embodiment of an embodiment of a system 11 associated with a surgical implant device (having a generally flat distal end) 71 and an interface device 41 that is positioned over a guide member 61, and a biomaterial and/or biologically active agents delivery device 21.

Figure 3:
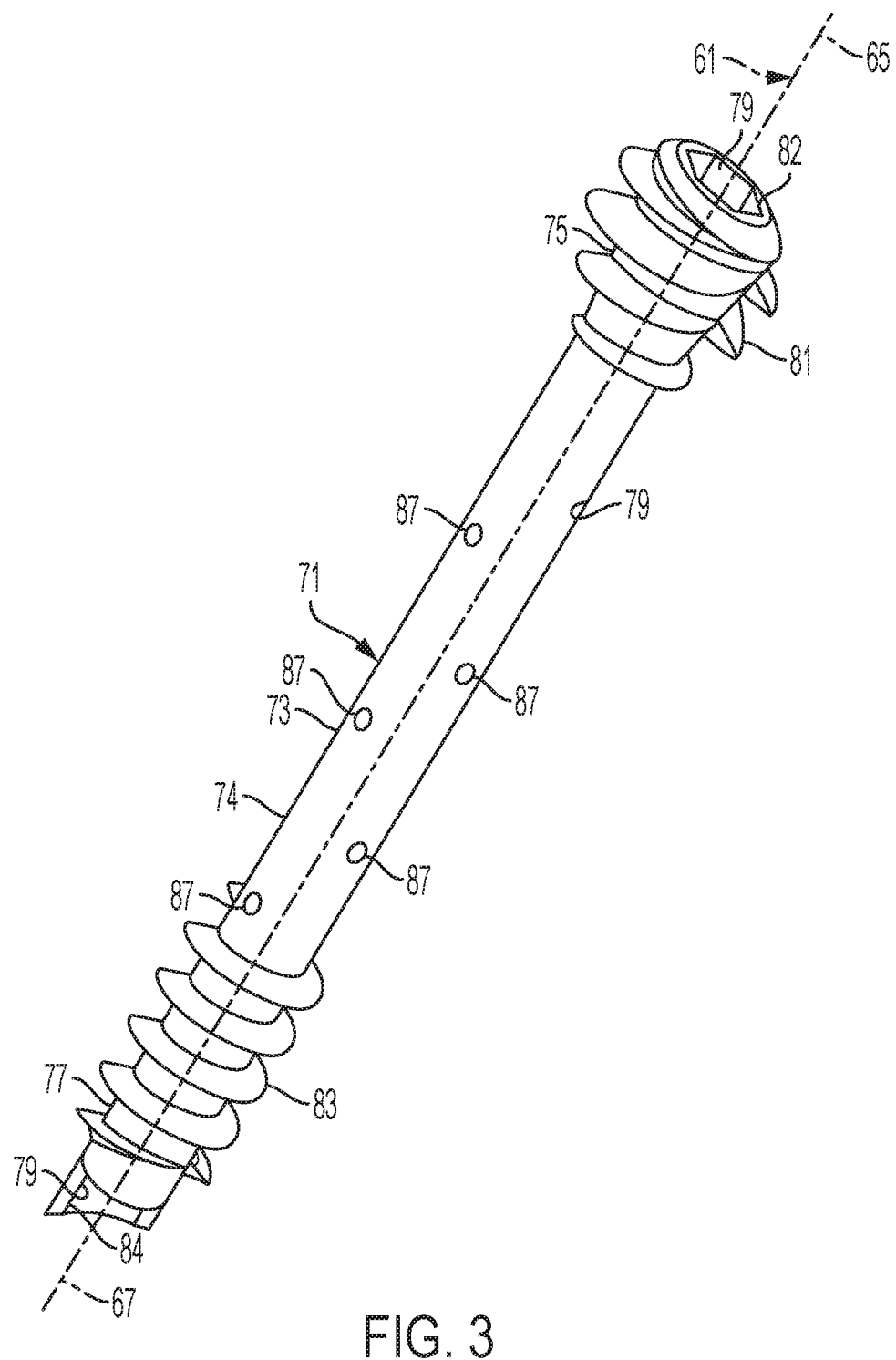
FIG. 3 schematically illustrates an embodiment an embodiment of the surgical implant device (having a generally tapered distal end).

FIG. 3 schematically illustrates an embodiment an embodiment of the surgical implant device (having a generally tapered distal end) 71.

Figure 4:
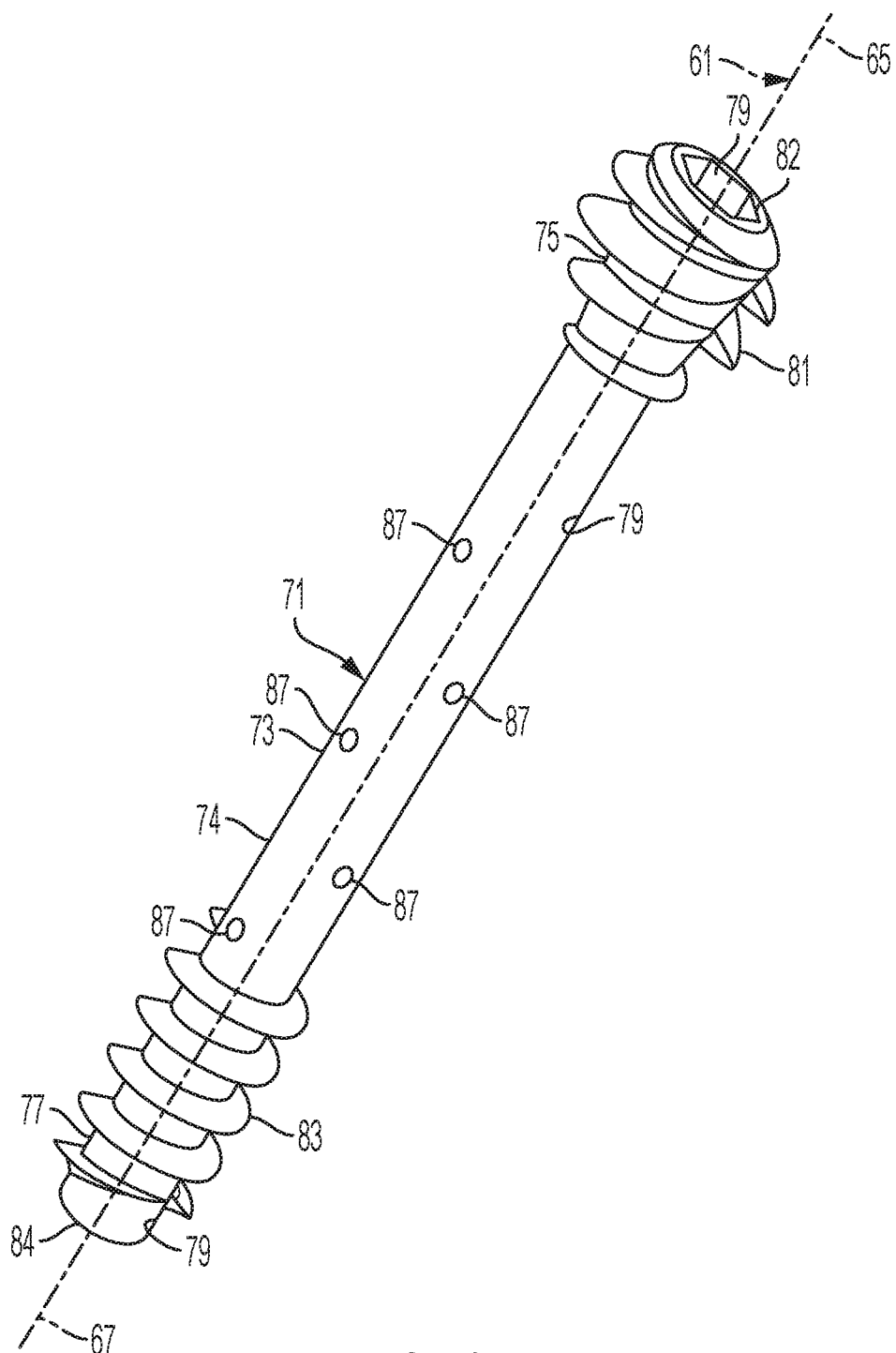
FIG. 4 schematically illustrates an embodiment an embodiment of the surgical implant device (having a generally flat distal end).

FIG. 4 schematically illustrates an embodiment an embodiment of the surgical implant device (having a generally flat distal end) 71 and illustrates a hexagonal-shaped surgical implant device bore proximal opening 82 to form a socket (e.g., female fitting feature).

Figure 5:
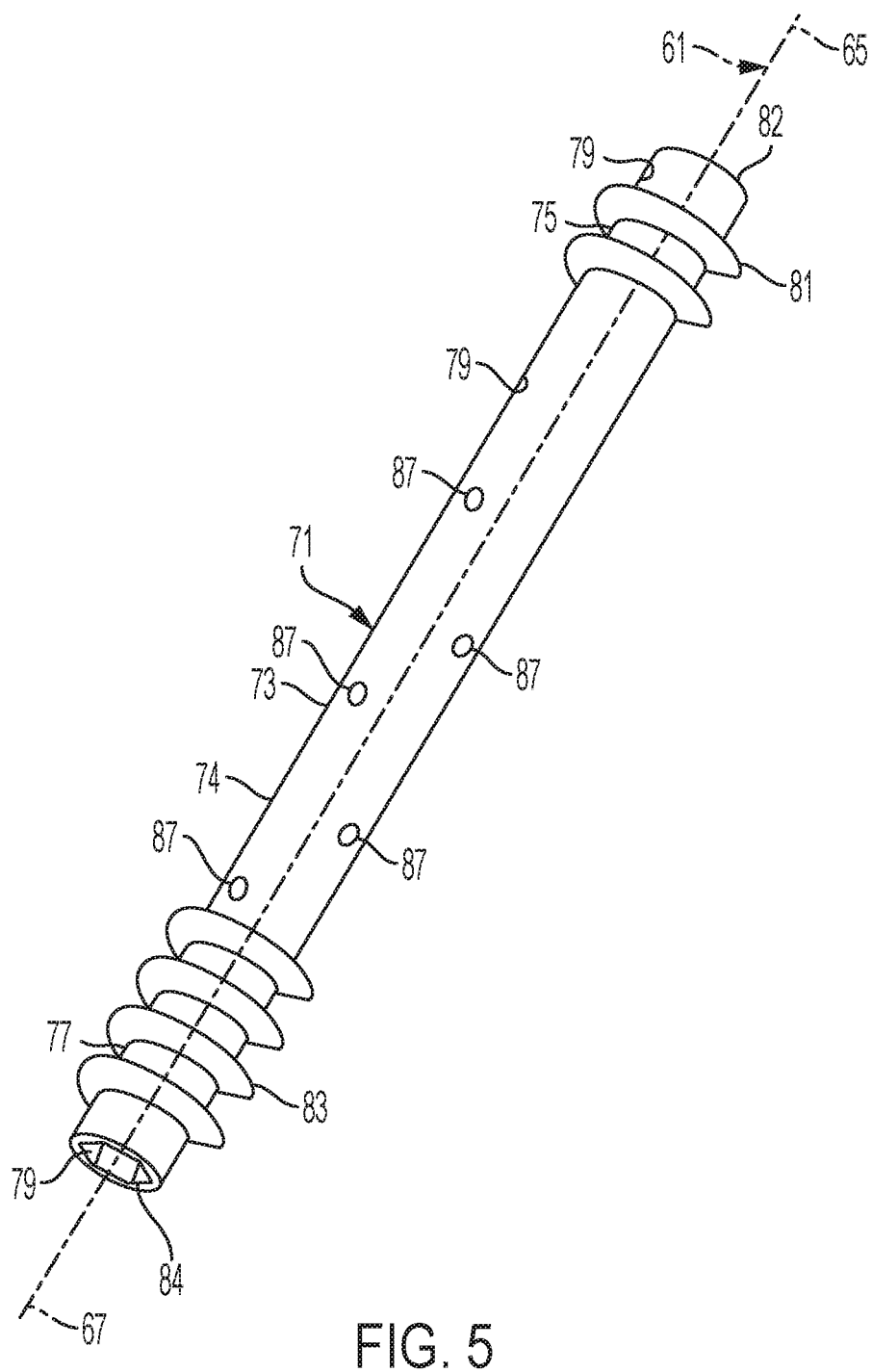
FIG. 5 schematically illustrates an embodiment an embodiment of the surgical implant device (having a generally flat distal end) and illustrates a hexagonal-shaped surgical implant device bore distal opening to form a socket.

FIG. 5 schematically illustrates an embodiment an embodiment of the surgical implant device (having a generally flat distal end) 71 and illustrates a hexagonal-shaped surgical implant device bore distal opening 84 to form a socket (e.g., female fitting feature).

In any of the embodiments disclosed herein, an implant device 71 may be implemented with a hexagonal-shaped surgical implant device bore opening at both ends of the surgical implant device 71. As such, the surgical implant device 71 may include a hexagonal-shaped surgical implant device bore proximal opening 82 to form a socket (e.g., female fitting feature) and a hexagonal-shaped surgical implant device bore distal opening 84 to form a socket (e.g., female fitting feature). The socket may be any polygon shape (e.g., pentagon, rectangular, etc.) or recess forming a female feature. Conversely, the ends may be of a male fitting feature to communicate or mate with associated proximal linking components of the system 11 that would be of female fitting design. With sockets, female-male fittings, or male-female fittings (or the like) on both ends of the surgical implant device 71 it provides the user more flexibility and possibilities for advancing or withdrawing the surgical implant device 71 in either or both directions. With sockets, female-male fittings, or male-female fittings (or the like) on both ends of the surgical implant device 71 it provides the user greater flexibility and possibilities in achieving access to and contact with the surgical implant device 71. Moreover, if the surgical implant device 71 should break or separate then the user would have the flexibility of removing each separated, broken section of the surgical implant device 71 from either of the respective ends (i.e., at both of the remaining broken sections associated with the proximal and distal ends).

Figure 6:
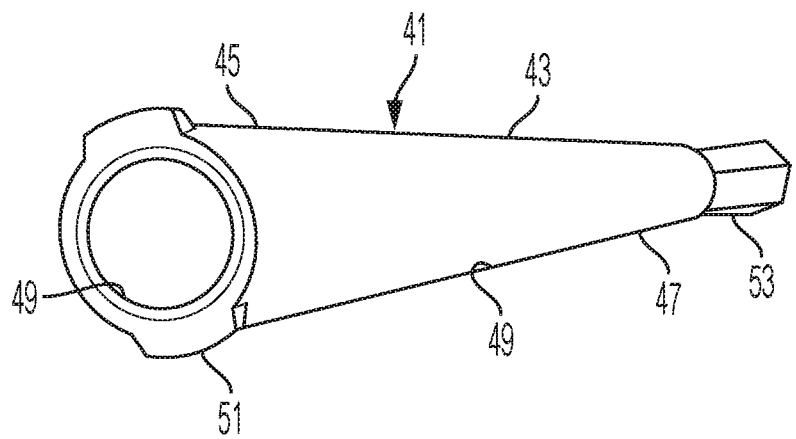
FIG. 6 schematically illustrates a perspective view of an embodiment an interference device having a male-fitting hexagonal-shaped interference device distal end.

FIG. 6 schematically illustrates a perspective view of an embodiment an interference device 41 having a male-fitting hexagonal-shaped interference device distal end 47.

Figure 7:
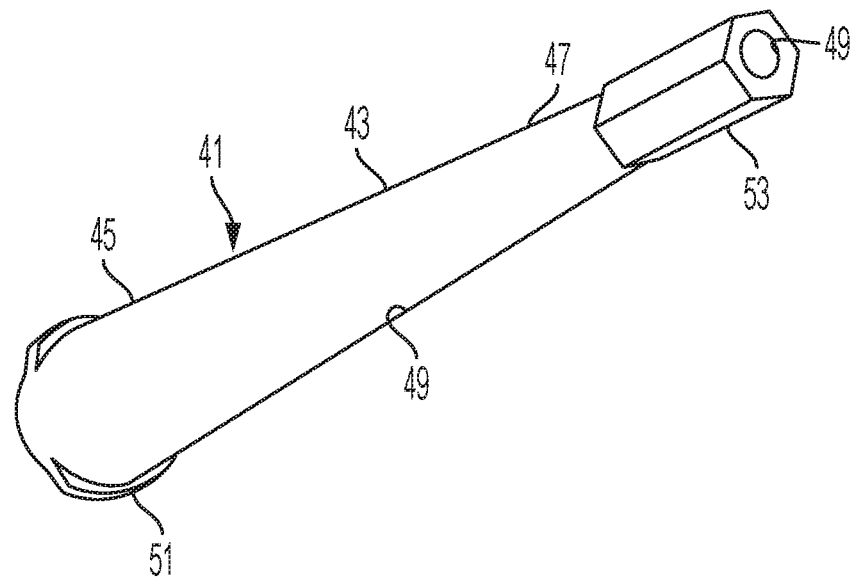
FIG. 7 schematically illustrates a perspective view of an embodiment an interference device having a male-fitting hexagonal-shaped interference device distal end.

FIG. 7 schematically illustrates a perspective view of an embodiment an interference device 41 having a male-fitting hexagonal-shaped interference device distal end 47.

Figure 8:
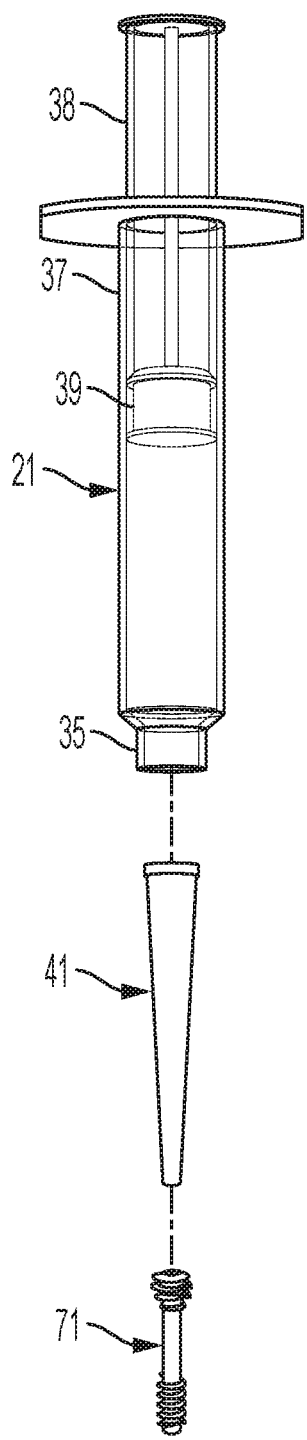
FIG. 8 schematically illustrates an exploded view of an embodiment of the surgical implant device, an interface device, and biomaterial and/or biologically active agents delivery device.

FIG. 8 schematically illustrates an exploded view of an embodiment of a system 11 associated with a surgical implant device 71, an interface device 41, and biomaterial and/or biologically active agents delivery device 21.

Figure 9:
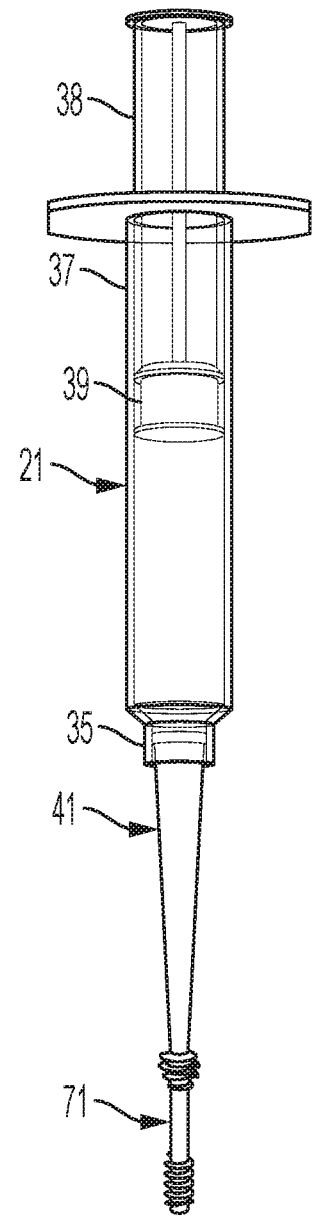
FIG. 9 schematically illustrates an assembled view of an embodiment an embodiment of the surgical implant device, an interface device, and biomaterial and/or biologically active agents delivery device.

FIG. 9 schematically illustrates an assembled view of an embodiment of a system 11 associated with a surgical implant device 71, an interface device 41, and biomaterial and/or biologically active agents delivery device 21.

Figure 10:
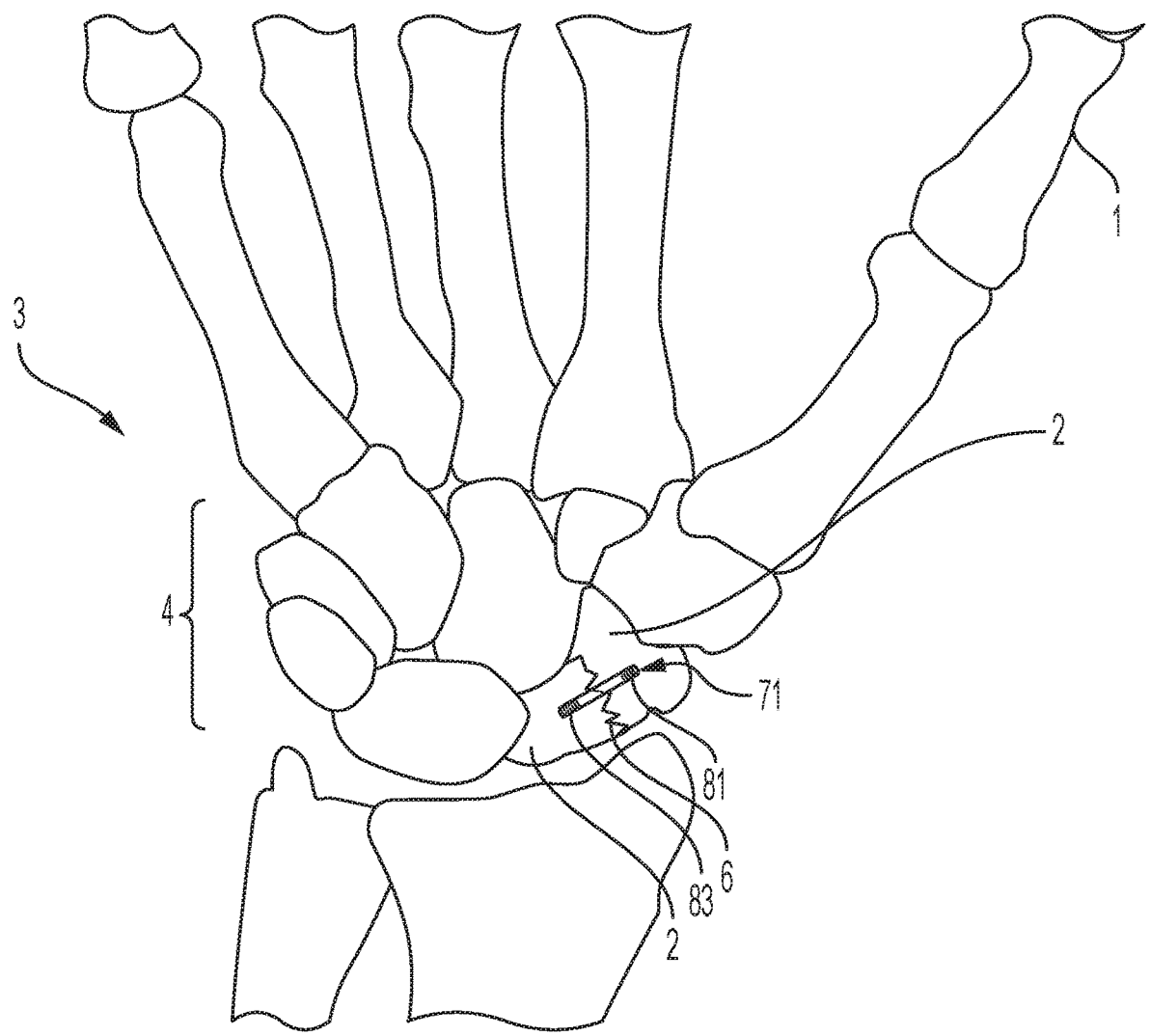
FIG. 10 schematically illustrates an embodiment an embodiment of the surgical implant device in place at the fracture of the target site or region being one of the carpal bones.

FIG. 10 schematically illustrates an embodiment an embodiment of the surgical implant device 71 in place at the fracture 6 of the target site or region 2 being one of the carpal bones (which could otherwise be any bone). In other applications it may be at a joint space 6 between two bones.

Figure 11:
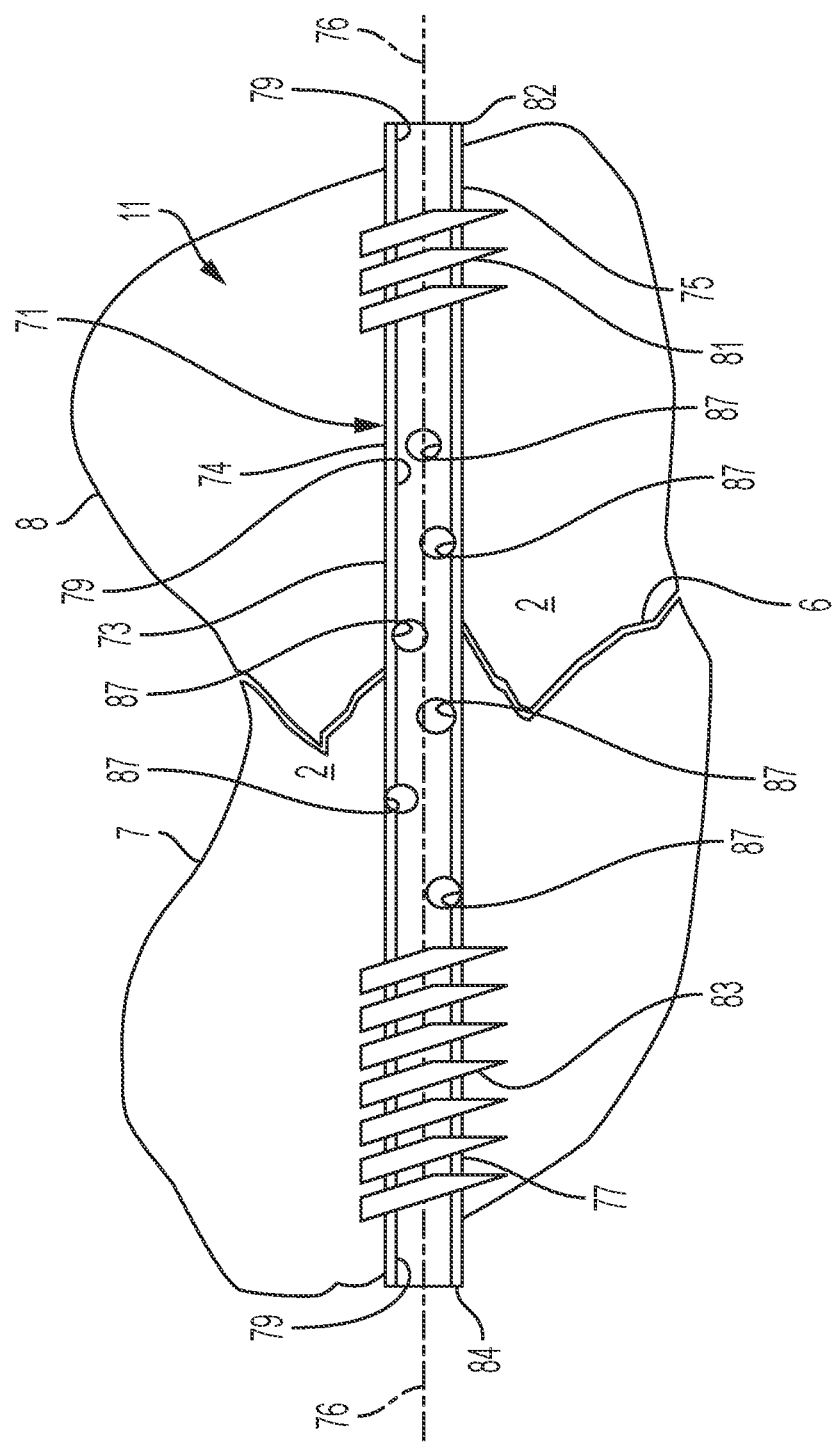
FIG. 11 schematically illustrates an embodiment of the surgical implant device in place at the fracture or joint space of the target site or region without a guide member present.

FIG. 11 schematically illustrates an embodiment of a system 11 including the surgical implant device in place at the fracture 6 or joint space 6 of the target site or region 2 without a guide member present.

Figure 12:
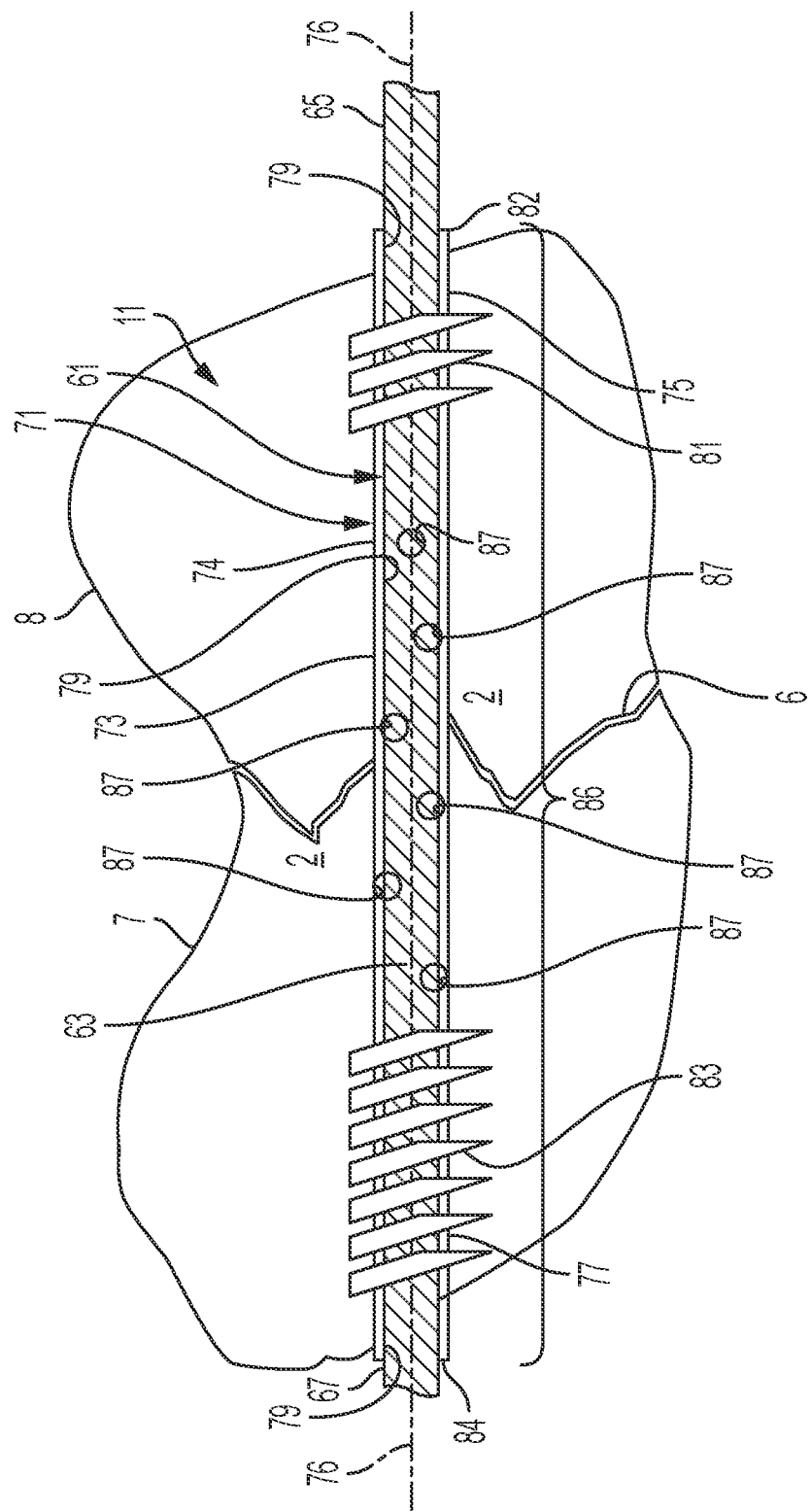
FIG. 12 schematically illustrates an embodiment of the surgical implant device in place at the fracture or joint space of the target site or region and positioned over a guide member which occludes the plurality of apertures.

FIG. 12 schematically illustrates an embodiment of a system 11 including the surgical implant device 71 in place at the fracture or joint space 6 of the target site or region 2 and positioned over a guide member 61 which occludes the plurality of apertures 87.

Figure 13:
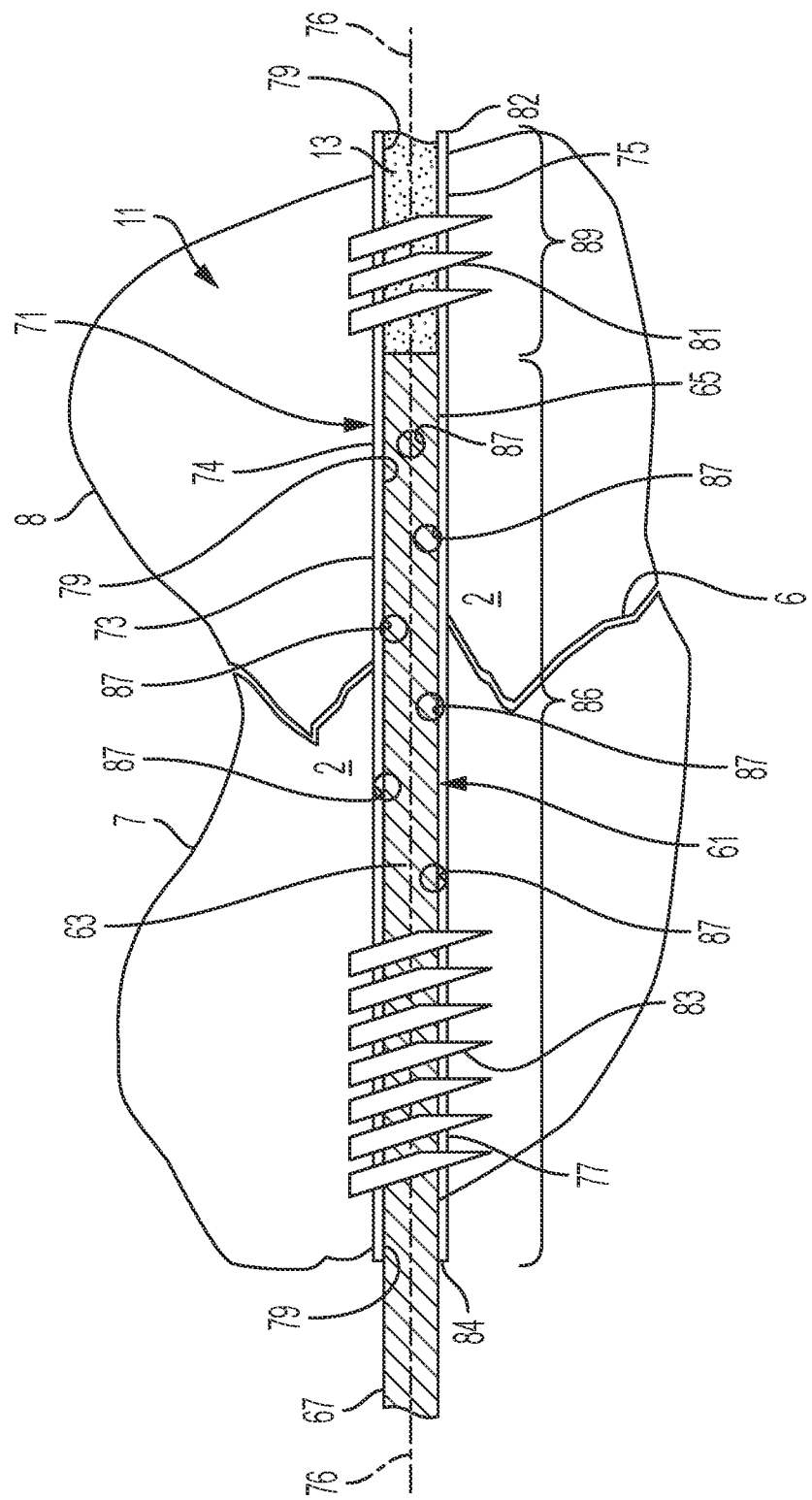
FIG. 13 schematically illustrates an embodiment of the surgical implant device in place at the fracture or joint space of the target site or region and positioned over a guide member which occludes the plurality of apertures, and wherein the guide member has been advanced in a distal direction and the biomaterial and/or biologically active agents is provided in the surgical implant device bore.

FIG. 13 schematically illustrates an embodiment of a system 11 including the surgical implant device 71 in place at the fracture or joint space 6 of the target site or region 2 and positioned over a guide member 61 which occludes the plurality of apertures 87, and wherein the guide member 61 has been advanced in a distal direction and the biomaterial and/or biologically active agents 13 is provided in the surgical implant device bore 79 at the surgical implant device bore proximal opening 82.

Figure 14:
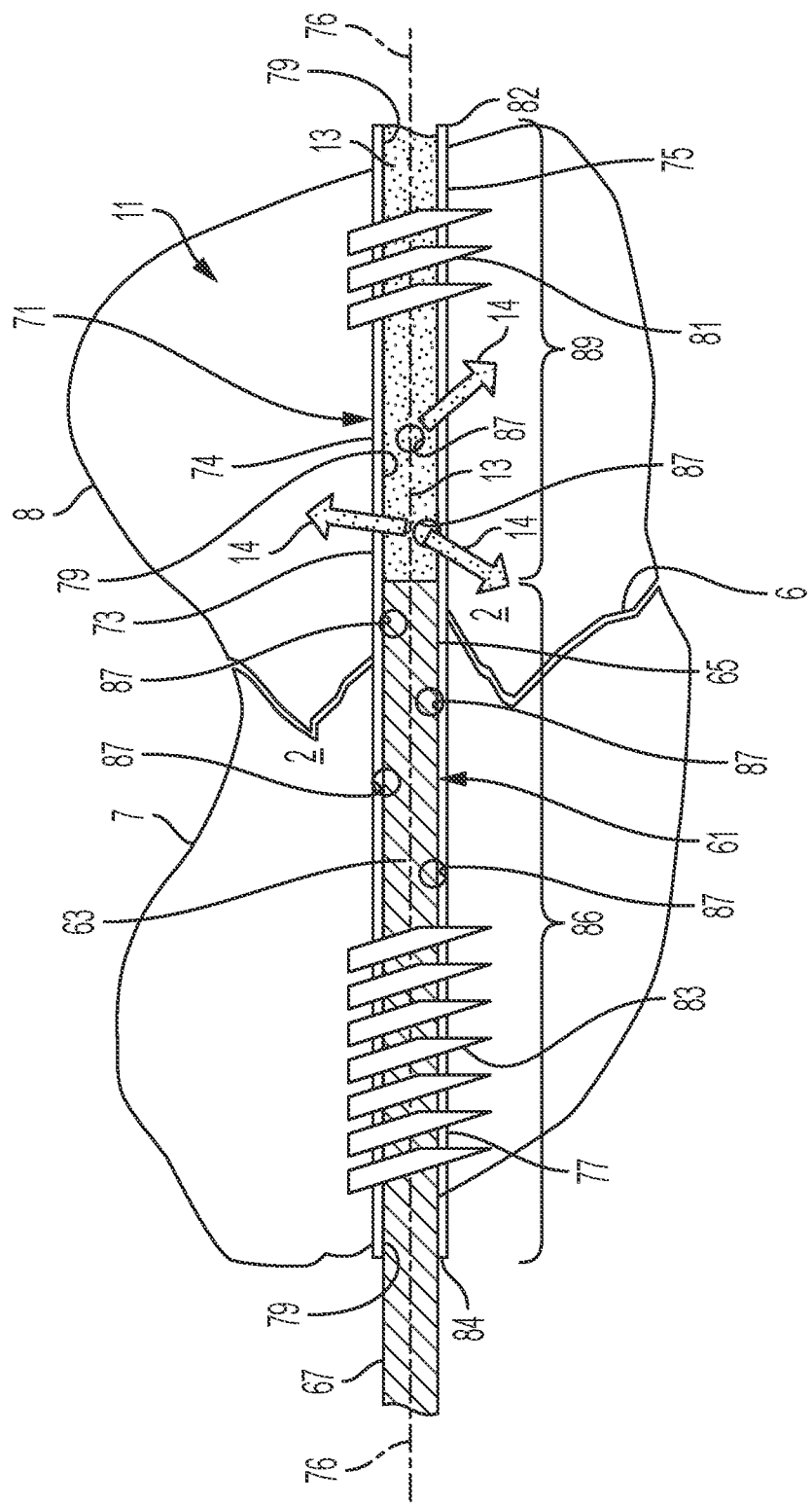
FIG. 14 schematically illustrates an embodiment of the surgical implant device in place at the fracture or joint space of the target site or region and positioned over a guide member which occludes some of the plurality of apertures, and wherein and the guide member has been further advanced in a distal direction (compared to FIG. 13) and the biomaterial and/or biologically active agents is provided in the surgical implant device bore of which is flowing from the plurality of apertures that are not occluded by guide member.

FIG. 14 schematically illustrates an embodiment of a system 11 including the surgical implant device 71 in place at the fracture or joint space 6 of the target site or region 2 and positioned over a guide member 61 which occludes some of the plurality of apertures 87, and wherein and the guide member 61 has been further advanced in a distal direction (compared to FIG. 13) and the biomaterial and/or biologically active agents 13 is provided in the surgical implant device bore 79 of which is flowing from the plurality of apertures 87 that are not occluded by guide member 61.

Figure 15:
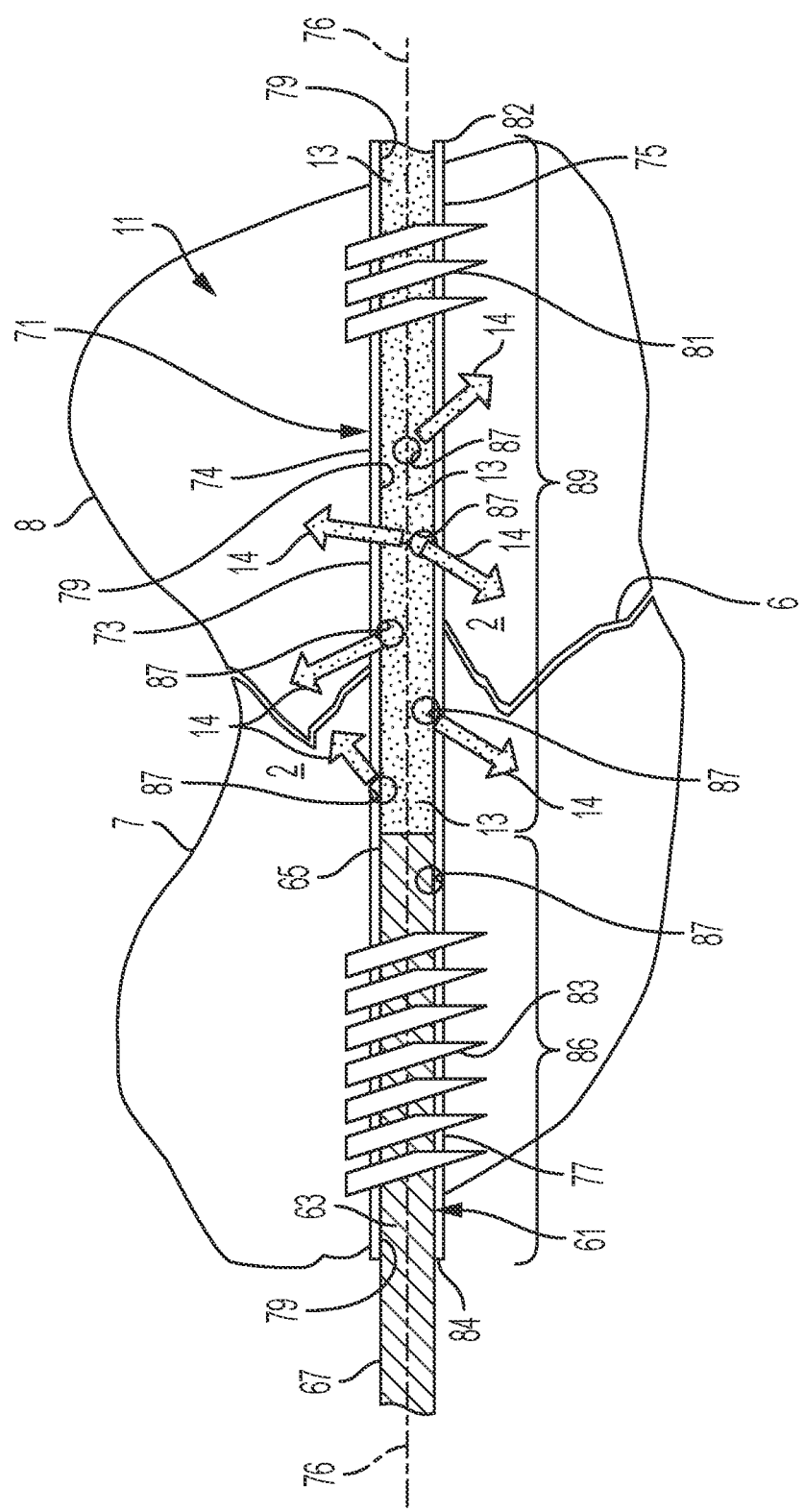
FIG. 15 schematically illustrates an embodiment of the surgical implant device in place at the fracture or joint space of the target site or region and positioned over a guide member which occludes some of the plurality of apertures, and wherein and the guide member has been further advanced in a distal direction (compared to FIG. 14) and the biomaterial and/or biologically active agents is provided in the surgical implant device bore of which is flowing from the plurality of apertures that are not occluded by guide member.

FIG. 15 schematically illustrates an embodiment of a system 11 including the surgical implant device 71 in place at the fracture or joint space 6 of the target site or region 2 and positioned over a guide member 61 which occludes some of the plurality of apertures 87, and wherein and the guide member 61 has been further advanced in a distal direction (compared to FIG. 14) and the biomaterial and/or biologically active agents 13 is provided in the surgical implant device bore 79 of which is flowing from the plurality of apertures 87 that are not occluded by guide member 61.

Figure 16:
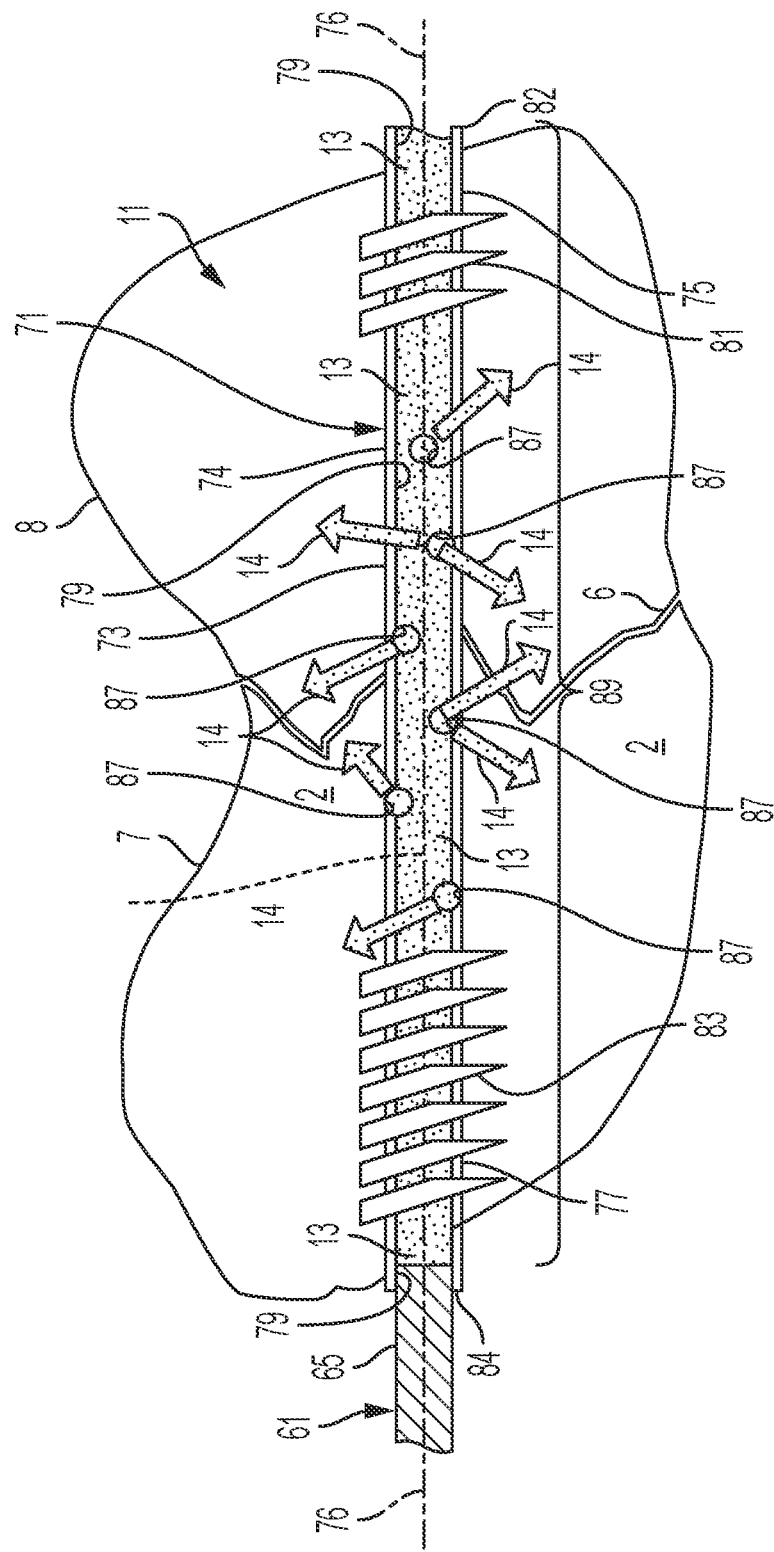
FIG. 16 schematically illustrates an embodiment of the surgical implant device in place at the fracture or joint space of the target site or region and positioned over a guide member which does not occlude any of the plurality of apertures, and wherein the guide member has been further advanced in a distal direction (compared to FIG. 15) and the biomaterial and/or biologically active agents is provided in the surgical implant device bore of which is flowing from all the plurality of apertures, being no longer occluded by guide member.

FIG. 16 schematically illustrates an embodiment of a system 11 including the surgical implant device 71 in place at the fracture or joint space 6 of the target site or region 2 and positioned over a guide member 61 which does not occlude any of the plurality of apertures 87, and wherein and the guide member 61 has been further advanced in a distal direction (compared to FIG. 15) and the biomaterial and/or biologically active agents 13 is provided in the surgical implant device bore 79 of which is flowing from all the plurality of apertures 87, being no longer occluded by guide member 61.

FIGS. 12-16 schematically indicate the guide member 61 advancing or withdrawing in the proximal to distal direction (right to left in the illustration). As such the biomaterial and/or biologically active agents 13 is provided in the surgical implant device bore 79 at the surgical implant device bore proximal opening 82. The surgical implant device bore distal opening 84 may be configured to be sealed by the guide member 61 while the guide member 61 is partially absent from the surgical implant device bore 79 thereby defining a guide member-absent bore area 89 in the surgical implant device bore to allow the biomaterial and/or biologically active agents 13 to extrude or diffuse from at least one of the apertures 87 (as schematically reflected by arrows, 14) located in the guide member-absent bore area 89 to the target region 2 of the subject 1. Also, in an embodiment or instance where the guide member 61 is present or occupying the surgical implant device bore 79, it thereby defines a guide member-occupied bore area 86.

Although not illustrated, it is also possible for the guide member 61 to advance or withdraw in the distal to proximal direction (left to right in the illustration). As such the biomaterial and/or biologically active agents 13 is provided in the surgical implant device bore 79 at the surgical implant device bore distal opening 84. The surgical implant device bore proximal opening 82 may be configured to be sealed by the guide member 61 while the guide member 61 is partially absent from the surgical implant device bore 79 thereby defining a guide member-absent bore area in the surgical implant device bore to allow the biomaterial and/or biologically active agents 13 to extrude or diffuse from at least one of the apertures 87 (as schematically reflected by arrows, 14) located in the guide member-absent bore area to the target region 2 of the subject 1. Accordingly, an aspect of an embodiment allows the user to manipulate the guide member 61 in either direction of the surgical implant device 71 providing flexibility in its use as well as range of coverage of biomaterial and/or biologically active agents 13.

Figure 17:
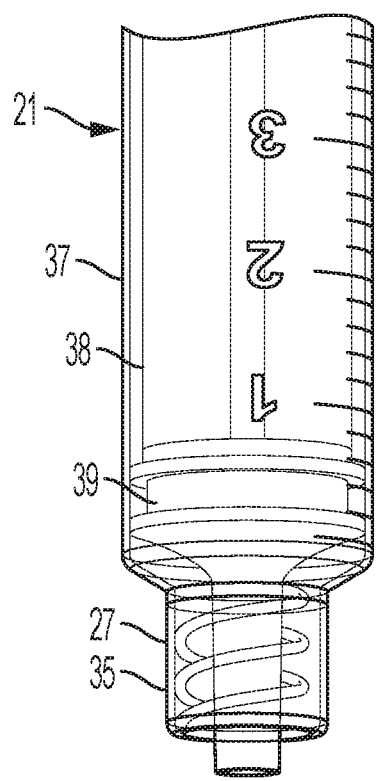
FIG. 17 schematically illustrates a perspective partial view of an embodiment of the biomaterial and/or biologically active agents delivery device, particularly at the biomaterial and/or biologically active agents delivery device distal end having a luer lock fitting.

FIG. 17 schematically illustrates a perspective partial view of an embodiment of the biomaterial and/or biologically active agents delivery device 21 (at least partially of a syringe device type design), particularly at the biomaterial and/or biologically active agents delivery device distal end 27 having a luer lock fitting 35. Also illustrated is the barrel of the delivery device 37, plunger of the delivery device 38, plunger seal of the delivery device 39.

Figure 18:
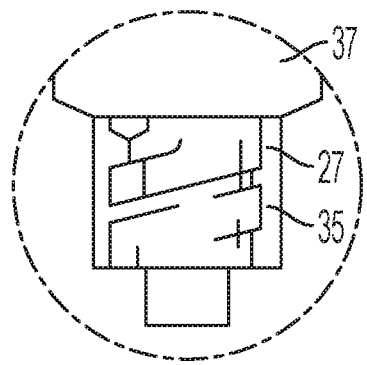
FIG. 18 schematically illustrates a schematic view of an embodiment of the biomaterial and/or biologically active agents delivery device, particularly at the biomaterial and/or biologically active agents delivery device distal end having a luer lock fitting.

FIG. 18 schematically illustrates a schematic view of an embodiment of the biomaterial and/or biologically active agents delivery device 21 (at least partially of a syringe device type design), particularly at the biomaterial and/or biologically active agents delivery device distal end 27 having a luer lock fitting 35 and barrel of the delivery device 37.

FIGS. 11-16 schematically illustrate an embodiment of the bone fixation system 11 for promoting the union of a bone fracture 6 or fusion of bones across a joint space 6 at a target region 2 of a subject. A surgical implant device 71 may include a surgical implant device proximal end 75, a surgical implant device distal end 77 and a surgical implant device longitudinal member 73 there between and a surgical implant device bore 79 running longitudinally there through the surgical implant device longitudinal member 73 along its longitudinal axis 76. The surgical implant device bore 79 may include a surgical implant device bore proximal opening 82 on the longitudinal axis 76 and a surgical implant device bore distal opening 84 on the longitudinal axis 76. The surgical implant device 71 may also include a plurality of apertures 87 disposed on the surgical implant device longitudinal member 73 providing a fluidic passage between an outer surface 74 of the surgical implant device longitudinal member 73 and the surgical implant device bore 79. The surgical implant device bore proximal opening 82 may be configured to provide a fluidic passage for biomaterial and/or biologically active agents material 13 therein. The surgical implant device bore 79 may be configured to receive and advance a guide member 61 therein. The surgical implant device bore distal opening 84 may be configured to be sealed by the guide member 61 that is disposed in said surgical implant device bore distal opening 84 while the guide member 61 is partially absent from the surgical implant device bore 79 thereby defining a guide member-absent bore area 89 in the surgical implant device bore to allow the biomaterial and/or biologically active agents 13 to extrude or diffuse from at least one of the apertures 87 (as schematically reflected by arrows, 14) located in the guide member-absent bore area 89 to the target region 2 of the subject 1. Also, in an embodiment or instance where the guide member 61 is present or occupying the surgical implant device bore 79, it thereby defines a guide member-occupied bore area 86.

In an embodiment of the system 11 the surgical implant device bore 79 may be configured to become coaxially aligned at its surgical implant device bore proximal opening 82 relative to the guide member 61 to allow the guide member 61 to travel inside the surgical implant device bore 79.

In an embodiment of the system 11 the surgical implant device bore 79 may be configured to become coaxially aligned at its surgical implant device bore distal opening 84 relative to the guide member 61 to allow the guide member 61 to travel inside the surgical implant device bore 79.

In an embodiment of the system 11 the surgical implant device proximal end 75 may be accessed percutaneously. In an embodiment the surgical implant device proximal end 75 may be accessed endoscopically. In an embodiment the surgical implant device proximal end 75 may be accessed both percutaneously and endoscopically.

FIGS. 1-5 schematically illustrate aspects of embodiments of the bone fixation system 11 that may further include a surgical implant device attachment and sealant mechanism 85 disposed on the surgical implant device proximal end 75. In an embodiment, the surgical implant device attachment and sealant mechanism 85, the surgical implant device bore 79, and the plurality of apertures 87 are configured to provide a fluidic passage for biomaterial and/or biologically active agents material to travel through the surgical implant device attachment and sealant mechanism 85, the surgical implant device bore 79, and the plurality of apertures 87 to allow the biomaterial and/or biologically active agents to extrude or diffuse from at least one of the apertures 87 to the target region 2 of the subject 1.

An embodiment of the bone fixation system 11 may further include an interface device 41 which may include an interface device proximal end 45, an interface device distal end 47 and an interface device longitudinal member 43 there between and an interface device bore 49 running longitudinally there through; and wherein the interface device 41 is configured to provide a fluidic passage for the biomaterial and/or biologically active agents to travel through the interface device 41 to the surgical implant device 71.

Referring to FIGS. 1-5, an embodiment of the bone fixation system 11 may further include an interface device 41 that may include an interface device proximal end 45, an interface device distal end 47 and an interface device longitudinal member 43 there between and an interface device bore 49 running longitudinally there through. In an embodiment, the interface device 41 may include an interface device proximal attachment and sealant mechanism 51 disposed on the interface device the proximal end 45. In an embodiment, the interface device 41 may include an interface device distal attachment and sealant mechanism 53 disposed on the interface device the distal end 47. In an embodiment, the interface device distal attachment and sealant mechanism 53 may be configured to fasten to the surgical implant device attachment and sealant mechanism 85 to provide a fixed and fluidic type sealed connection thereto. Accordingly, the interface device proximal attachment and sealant mechanism 51, the interface device bore 49, the interface device distal attachment and sealant mechanism 53 are configured to provide a fluidic passage for the biomaterial and/or biologically active agents to travel through the interface device proximal attachment and sealant mechanism 51, the interface device bore 41, the interface device distal attachment and sealant mechanism 53 to the surgical implant device attachment and sealant mechanism 85 of the surgical implant device 71.

An embodiment of the bone fixation system 11 may further include a biomaterial and/or biologically active agents delivery device 21, that may include a biomaterial and/or biologically active agents delivery device proximal end 2, a biomaterial and/or biologically active agents delivery device distal end 27 and a biomaterial and/or biologically active agents delivery device longitudinal member 23 there between and an biomaterial and/or biologically active agents delivery device bore 29 running longitudinally there through; and wherein the biomaterial and/or biologically active agents delivery device 21 is configured to provide a fluidic passage for the biomaterial to travel through the biomaterial and/or biologically active agents delivery device to the an interface device 41 and eventually onto the surgical implant device 71.

Referring to FIGS. 1-5, an embodiment of the bone fixation system 11 may further include an biomaterial and/or biologically active agents delivery device 21 that may include an biomaterial and/or biologically active agents delivery device proximal end 25, a biomaterial and/or biologically active agents delivery device distal end 27 and a biomaterial and/or biologically active agents delivery device longitudinal member 23 there between and an biomaterial and/or biologically active agents delivery device bore 29 running longitudinally there through. In an embodiment, the biomaterial and/or biologically active agents delivery device 21 may include a biomaterial and/or biologically active agents delivery distal device attachment and sealant mechanism 33 disposed on the biomaterial and/or biologically active agents delivery device distal end 27. In an embodiment, the biomaterial and/or biologically active agents delivery distal attachment and sealant mechanism 33 may be configured to fasten to the interface device proximal attachment and sealant mechanism 51 to provide a fixed and fluid type sealed connection thereto. Accordingly, the biomaterial and/or biologically active agents delivery device bore 29 and the biomaterial and/or biologically active agents delivery device distal attachment and sealant mechanism 33 are configured to provide a fluidic passage for the biomaterial and/or biologically active agents to travel through the biomaterial and/or biologically active agents delivery device bore 29 and the biomaterial and/or biologically active agents delivery device distal attachment and sealant mechanism 33 to the interface device proximal attachment and sealant mechanism 51.

In an embodiment the surgical implant device attachment and sealant mechanism 85 is a male to female type fitting. Male to female can be either arrangement such that the distal end 75 includes a female component or male component. For example, in an embodiment, the surgical implant device attachment and sealant mechanism 85 may include one or more of the following: male to female friction connector, male to female friction connection, ridge/valley connection, snap/click connection, O-ring connection, screw/twist type mechanisms, clearance fit connection, location or transition fit connection, and interference fit connection.

In an embodiment the interface device distal attachment and sealant mechanism 53 is a male to female type fitting. Male to female can be either arrangement such that the distal end 75 includes a female component or male component. For example, in an embodiment, the interface device distal attachment and sealant mechanism 53 may include one or more of the following: male to female friction connector, male to female friction connection, ridge/valley connection, snap/click connection, O-ring connection, screw/twist type mechanisms, clearance fit connection, location or transition fit connection, and interference fit connection.

In an embodiment the interface device proximal attachment and sealant mechanism 51 is a male to female type fitting. Male to female can be either arrangement such that the distal end 75 includes a female component or male component. For example, in an embodiment, the interface device proximal attachment and sealant mechanism 51 may include one or more of the following: male to female friction connector, male to female friction connection, ridge/valley connection, snap/click connection, O-ring connection, screw/twist type mechanisms, clearance fit connection, location or transition fit connection, Luer Lock fitting, and interference fit connection.

In an embodiment the biomaterial and/or biologically active agents delivery distal attachment and sealant mechanism 33 is a male to female type fitting. Male to female can be either arrangement such that the distal end 75 includes a female component or male component. For example, in an embodiment, the biomaterial and/or biologically active agents delivery distal attachment and sealant mechanism 33 may include one or more of the following: male to female friction connector, male to female friction connection, ridge/valley connection, snap/click connection, O-ring connection, screw/twist type mechanisms, clearance fit connection, location or transition fit connection, Luer Lock fitting, and interference fit connection.

Referring to FIG. 5, an embodiment may include a distal end 77 of the of the surgical implant device 71 that includes a male to female type fitting, such as the hexagonal socket defined by the distal bore opening. Male to female can be either arrangement such that the distal end 75 includes a female component or male component. For example, in an embodiment, the male to female fitting may be configured as distal attachment and sealant mechanism, which may include one or more of the following: male to female friction connector, male to female friction connection, ridge/valley connection, snap/click connection, O-ring connection, screw/twist type mechanisms, clearance fit connection, location or transition fit connection, Luer Lock fitting, and interference fit connection.

Referring to FIGS. 1-5, an embodiment of the surgical implant device 71 may further include a distal section of threads 83 disposed at the surgical implant device distal end 77. In an embodiment of the bone fixation system 11 may further include a proximal section of threads 81 disposed from at the surgical implant device proximal end 75.

Referring to FIGS. 1-5 and 8-16, the surgical implant device 71 may be any one of the following: dowel, screw, tack, pin, nail, rivet, or the like. In an embodiment, the screw may be anyone of the following: a compression screw, fixation screw, cancellous screw, cortical screw, machine screw, or the like.

Referring to FIGS. 1-5 and 8-16, the apertures 87 of the surgical implant device 71 may be one or more of any combination of the following: following: fenestration, slot, gap, slit, hole, perforation, or the like. In an embodiment, at least one of the plurality of apertures 87 may have a length or diameter of a size of one or more of the following dimensions: about 0.1 mm, about 0.2 mm, about 0.3 mm, about 0.4 mm, about 0.5 mm, about 0.6 mm about 0.7 mm, about 0.8 mm, or about 0.9 mm. It should be appreciated that the length and diameter may be less than or greater than as listed. It should be appreciated that the length and diameter of the aperture 87 may be sized according to the size of the surgical implant device 71 and according to the size of target site or region 2. It should be appreciated that the number apertures 87 may be selected according to the size of the surgical implant device 71 and according to the size of target site or region 2. It should be appreciated that the size of the surgical implant device may be sized according to the size of target site or region 2. It should be appreciated that the size of the interface device may be sized according to the size of target site or region 2. In an embodiment, the number of the plurality of apertures 87 include at a range of the following: about 3 to about 30. It should be appreciated that the number of apertures may be less than or greater than as listed.

Referring to FIGS. 1-5 and 8-16, the surgical implant device bore 79 may have a longitudinal length from about 5 mm to about 50 mm; the surgical implant device bore 79 may have an internal diameter of about 0.5 to about 5.5 mm; the surgical implant device longitudinal member 73 may have an external diameter of about 2 mm to about 15 mm. It should be appreciated that the lengths and diameters may be less than or greater than as listed.

Referring to FIGS. 1-5 and 8-16, the interface device bore 49 may have an inner diameter at the interface device proximal end 45 of about 4.75 mm; and the interface device bore 49 may have an inner diameter at the interface device distal end 47 of about 1.1 mm. It should be appreciated that the inner and outer diameters may be less than or greater than as listed.

In an embodiment, the biomaterial or biologically active agents may include structure component (e.g., scaffold or scaffold structure) or signaling component, respectively. In an embodiment the biomaterial or biologically active agents may include one or more any combination of the following: bone substitute, bone cement, infection preventative agent, biologics, antibiotics, bone morphogenic proteins, hydrogels, and hydrogel microspheres, scaffold, scaffold components, cytokines, and chemokines.

In an embodiment, the target region 2 for union of a bone fracture includes at least one of the following bones: carpal bone; scaphoid, tibia, fibula, femur, vertebra, clavicle, scapula, humerus, radius, ulna, ribs, sacrum, pubis, sternum, cranium, or any other bone.

In an embodiment, the wherein target region 2 for the fusion of bones across a joint space, such as for arthrodesis, or similar to arthrodesis, or the like, includes at least one of the following bones: carpal bone; scaphoid, tibia, fibula, femur, vertebra, clavicle, scapula, humerus, radius, ulna, ribs, sacrum, pubis, sternum, cranium, or any other bone or joint space.

An aspect of an embodiment of the present invention, provides a method for promoting the union of a bone fracture 6 and/or fusion of bones across a joint space 6 at a target region 2 of a subject 1. The method may include: inserting a surgical implant device 71 at the target region 2. In an embodiment, the surgical implant device 71 may include: a surgical implant device proximal end 75, a surgical implant device distal end 77 and a surgical implant device longitudinal member 73 there between and a surgical implant device bore 79 running longitudinally there through the surgical implant device longitudinal member 73 along its longitudinal axis 76. The surgical implant device bore 79 may include a surgical implant device bore proximal opening 82 on the longitudinal axis 76 and a surgical implant device bore distal opening 84 on the longitudinal axis 76. Moreover, in an embodiment, the surgical implant device 71 may include: a plurality of apertures 87 disposed on the surgical implant device longitudinal member 73 providing a fluidic passage between an outer surface 74 of the surgical implant device longitudinal member 73 and the surgical implant device bore 79. Still yet, in an embodiment, the surgical implant device 71 may include surgical implant device bore opening being configured to provide a fluidic passage for biomaterial material therein. Additionally, an aspect of the method may include following: providing a guide member 61 in the surgical implant device bore 79; sealing the surgical implant device bore distal opening 84 or surgical implant device bore proximal opening 82 with the guide member; and positioning the guide member relative to the surgical implant device to provide for the guide member to be partially absent from the surgical implant device bore thereby defining a guide member-absent bore area 89 in the surgical implant device bore to allow the biomaterial to extrude or diffuse from at least one of the apertures 87 located in the guide member-absent bore area to the target region 2 of the subject 1.

In an embodiment, the method may further include: attaching an interface device 41 in fluidic communication with the surgical implant device proximal end 75, wherein the interface device is configured to provide a fluidic passage for the biomaterial and/or biologically active agents to travel through the interface device to the surgical implant device. In an embodiment, attaching of the interface device with the surgical implant device proximal end 75 is implemented percutaneously. In an embodiment, the attaching of the interface device with the surgical implant device proximal end 75 is implemented endoscopically. In an embodiment, the attaching of the interface device with the surgical implant device proximal end 75 further includes fixedly rotating the surgical implant device. In an embodiment, the attaching of the interface device with the surgical implant device proximal end 75 further includes frictionally fitting into the surgical implant device.

In an embodiment, the method may further include: attaching an interface device 41 in fluidic communication with the surgical implant device distal end 77, wherein the interface device is configured to provide a fluidic passage for the biomaterial to travel through the interface device to the surgical implant device. In an embodiment, the attaching of the interface device with the surgical implant device distal end 77 is implemented percutaneously. In an embodiment, the attaching of the interface device with the surgical implant device distal end 77 is implemented endoscopically.

In an embodiment, the attaching of the interface device with the surgical implant device distal end 77 further includes fixedly rotating the surgical implant device. In an embodiment, the attaching of the interface device with the surgical implant device distal end 77 further includes frictionally fitting into the surgical implant device.

In an embodiment, the method may further include: fixedly rotating the surgical implant device 71 at the surgical implant device distal end 77. In an embodiment, the method may further include: attaching a biomaterial and/or biologically active agents_delivery device in fluidic communication with the interface device.

An aspect of an embodiment of the present invention, provides a method for promoting the union of a bone fracture 6 and/or fusion of bones across a joint space 6 at a target region 2 of a subject 1. The may method may include, among other activities, the following: inserting a guide member such as guide wire; boring a channel in the bone using a drill (such as a cannulated drill over the guide member); installing the surgical implant device (such as a cannulated screw) over the guide member and into the bored channel; applying the biomaterial and/or biologically active agents into bore of the surgical implant device. The method may further include advancing or withdrawing the guide member so as to seal the distal end or proximal end of the surgical implant device so as to redirect the flow out of the plurality of apertures that are not occluded by the guide member. The method may further include applying fluoroscopy imaging or other imaging modality during the aforementioned steps, process or activities. Referring to FIGS. 1 and 2, for example, an imaging apparatus 9 may be provided for the bone fixation system 11 or portions of the bone fixation system 11. It is noted that the guide member (e.g. guide wire) may be inserted percutaneously. As an example, one can do an arthroscopy of a joint and watch the percutaneously placed guide member (e.g. guide wire) cross the joint. In an embodiment, the guide member may sealed sufficiently enough at the distal end or proximal end of the surgical implant device so as to redirect the flow of the biomaterial and/or biologically active agents out of the plurality of apertures while not leaking at the sealed end(s). The differently, sealed sufficiently so as the path of least resistance of the flowing biomaterial and/or biologically active agents is through the apertures (rather than the end(s)).

In an embodiment, if some leakage is acceptable at the end(s) then there could be allowed some tolerance for leakage at the end(s) to a determined or specific magnitude.

An aspect of an embodiment provides the ability to implement the application biomaterial and/or biologically active agents into bore of the surgical implant device percutaneously. Percutaneous procedure is considered the least invasive intervention. Whereas the current methods and devices require the delivery of the biomaterial with a higher invasiveness, disruption of anatomy, and severity of surgery.

The present inventor notes that the bone is typically drilled first. There are some smaller self-drilling self-tapping screws but usually the torque required to place the screw in hard bone is too great without predrilling.

In an embodiment, the guide member may be a guide wire, pin, needle, other medical instrument, material or device, or the like.

EXAMPLES

Practice of an aspect of an embodiment (or embodiments) of the invention will be still more fully understood from the following examples, which are presented herein for illustration only and should not be construed as limiting the invention in any way.

Example 1. A bone fixation system for promoting the union of a bone fracture and fusion of bones across a joint space at a target region of a subject, said system comprising:
  a surgical implant device, comprising a surgical implant device proximal end, a surgical implant device distal end and a surgical implant device longitudinal member there between and a surgical implant device bore running longitudinally there through said surgical implant device longitudinal member along its longitudinal axis, said surgical implant device bore comprising a surgical implant device bore proximal opening on said longitudinal axis and a surgical implant device bore distal opening;
  a plurality of apertures disposed on said surgical implant device longitudinal member providing a fluidic passage between an outer surface of said surgical implant device longitudinal member and said surgical implant device bore;
  said surgical implant device bore proximal opening being configured to provide a fluidic passage for biomaterial material and/or biologically active agents therein;
  said surgical implant device bore, said surgical implant device bore distal opening, and said surgical implant device bore proximal opening being configured to be inserted over a guide member and a to have the guide member advanced or retracted therein said surgical device bore; and
  said surgical implant device bore distal opening being configured to be sealed by the guide member disposed in said surgical implant device bore distal opening while said guide member is partially absent from said surgical implant device bore thereby defining a guide member-absent bore area in said surgical implant device bore to allow the biomaterial and/or biologically active agents to extrude or diffuse from at least one of said apertures located in the guide member-absent bore area to the target region of the subject.

Example 2. The system of example 1, further comprising:
a) said surgical implant device bore distal opening being configured to provide a fluidic passage for biomaterial material and/or biologically active agents_therein; and said surgical implant device bore proximal opening being configured to be sealed by said guide member while said guide member is partially absent from said surgical implant device bore thereby defining a guide member-absent bore area in said surgical implant device bore to allow the biomaterial and/or biologically active agents to extrude or diffuse from at least one of said apertures located in the guide member-absent bore area to the target region of the subject; or
b) said surgical implant device bore distal opening being configured to allow said guide member to be removed from said surgical implant device bore through said surgical implant device bore distal opening.

Example 3. The system of example 1 (as well as subject matter in whole or in part of example 2), wherein said surgical implant device proximal end is configured to be accessed percutaneously.

Example 4. The system of example 1 (as well as subject matter of one or more of any combination of examples 2-3, in whole or in part), wherein said surgical implant device proximal end is configured to be accessed endoscopically.

Example 5. The system of example 1 (as well as subject matter of one or more of any combination of examples 2-4, in whole or in part), wherein said surgical implant device distal end is configured to be accessed percutaneously.

Example 6. The system of example 1 (as well as subject matter of one or more of any combination of examples 2-5, in whole or in part), wherein said surgical implant device distal end is configured to be accessed endoscopically.

Example 7. The system of example 1 (as well as subject matter of one or more of any combination of examples 2-6, in whole or in part), further comprising:
  a surgical implant device attachment and sealant mechanism disposed on said surgical implant device proximal end; and
  wherein said surgical implant device attachment and sealant mechanism, said surgical implant device bore, and said plurality of apertures are configured to provide a fluidic passage for biomaterial material and/or biologically active agents to travel through said surgical implant device attachment and sealant mechanism, said surgical implant device bore, and said plurality of apertures to allow the biomaterial and/or biologically active agents to extrude or diffuse from at least one of said apertures to the target region of the subject.

Example 8. The system of example 7 (as well as subject matter of one or more of any combination of examples 2-6, in whole or in part), further comprising:
  an interface device, comprising an interface device proximal end, an interface device distal end and an interface device longitudinal member there between and an interface device bore running longitudinally there through;
  an interface device proximal attachment and sealant mechanism disposed on said interface device said proximal end;
  an interface device distal attachment and sealant mechanism disposed on said interface device said distal end;
  said interface device distal attachment and sealant mechanism configured to fasten to said surgical implant device attachment and sealant mechanism to provide a fixed and fluidic type sealed connection thereto; and
  wherein said interface device proximal attachment and sealant mechanism, said interface device bore, said interface device distal attachment and sealant mechanism are configured to provide a fluidic passage for the biomaterial and/or biologically active agents to travel through said interface device proximal attachment and sealant mechanism, said interface device bore, said interface device distal attachment and sealant mechanism to said surgical implant device attachment and sealant mechanism.

Example 9. The system of example 1 (as well as subject matter of one or more of any combination of examples 2-8, in whole or in part), further comprising:
  an interface device, comprising an interface device proximal end, an interface device distal end and an interface device longitudinal member there between and an interface device bore running longitudinally there through; and
  wherein said interface device is configured to provide a fluidic passage for the biomaterial and/or biologically active agents to travel through said interface device to said surgical implant device.

Example 10. The system of example 8 (as well as subject matter of one or more of any combination of examples 2-7 and 9, in whole or in part), further comprising:
  a biomaterial and/or biologically active agents delivery device, comprising a biomaterial and/or biologically active agents delivery device proximal end, a biomaterial and/or biologically active agents delivery device distal end and a biomaterial and/or biologically active agents delivery device longitudinal member there between and a biomaterial and/or biologically active agents delivery device bore running longitudinally there through;

a biomaterial delivery and/or biologically active agents distal device attachment and sealant mechanism disposed on said biomaterial and/or biologically active agents delivery device distal end;

said biomaterial and/or biologically active agents delivery distal attachment and sealant mechanism configured to fasten to said interface device proximal attachment and sealant mechanism to provide a fixed and fluid type sealed connection thereto; and wherein said biomaterial and/or biologically active agents delivery device bore and said biomaterial and/or biologically active agents delivery device distal attachment and sealant mechanism are configured to provide a fluidic passage for the biomaterial and/or biologically active agents to travel through said biomaterial and/or biologically active agents delivery device bore and said biomaterial and/or biologically active agents delivery device distal attachment and sealant mechanism to said interface device attachment and sealant mechanism.

Example 11. The system of example 8 (as well as subject matter of one or more of any combination of examples 2-7 and 9-10, in whole or in part), further comprising:

a biomaterial and/or biologically active agents delivery device, comprising a biomaterial and/or biologically active agents delivery device proximal end, a biomaterial and/or biologically active agents delivery device distal end and a biomaterial and/or biologically active agents delivery device longitudinal member there between and a biomaterial and/or biologically active agents delivery device bore running longitudinally there through; and wherein said biomaterial and/or biologically active agents delivery device is configured to provide a fluidic passage for the biomaterial and/or biologically active agents to travel through said biomaterial and/or biologically active agents delivery device to said interface device.

Example 12. The system of example 7 (as well as subject matter of one or more of any combination of examples 2-6 and 8-11, in whole or in part), wherein:

said surgical implant device attachment and sealant mechanism is a male to female type fitting.

Example 13. The system of example 12 (as well as subject matter of one or more of any combination of examples 2-11, in whole or in part), wherein:

said interface device distal attachment and sealant mechanism is a male to female type fitting.

Example 14. The system of example 13 (as well as subject matter of one or more of any combination of examples 2-12, in whole or in part), wherein:

said interface device proximal attachment and sealant mechanism is a male to female type fitting.

Example 15. The system of example 14 (as well as subject matter of one or more of any combination of examples 2-13, in whole or in part), wherein:

said biomaterial and/or biologically active agents delivery distal attachment and sealant mechanism is male to female fitting.

Example 16. The system of example 13 (as well as subject matter of one or more of any combination of examples 2-12 and 14-15, in whole or in part), wherein:

said interface device distal attachment and sealant mechanism is a Luer Lock fitting.

Example 17. The system of example 16 (as well as subject matter of one or more of any combination of examples 2-15, in whole or in part), wherein:

said biomaterial and/or biologically active agents delivery distal attachment and sealant mechanism is a Luer Lock fitting.

Example 18. The system of example 1 (as well as subject matter of one or more of any combination of examples 2-17, in whole or in part), wherein:

said surgical implant device bore distal opening is configured as a male to female type fitting.

Example 19. The system of example 7 (as well as subject matter of one or more of any combination of examples 2-6 and 8-18, in whole or in part), wherein:

said surgical implant device bore distal opening is configured as a male to female type fitting.

Example 20. The system of example 1 (as well as subject matter of one or more of any combination of examples 2-19, in whole or in part), further comprising:

a distal section of threads disposed at said surgical implant device distal end.

Example 21. The system of example 20 (as well as subject matter of one or more of any combination of examples 2-19, in whole or in part), further comprising:

a proximal section of threads disposed at said surgical implant device proximal end.

Example 22. The system of example 1 (as well as subject matter of one or more of any combination of examples 2-21, in whole or in part), further comprising:

a proximal section of threads disposed at said surgical implant device proximal end.

Example 23. The system of example 1 (as well as subject matter of one or more of any combination of examples 2-22, in whole or in part), wherein said surgical implant device comprises a dowel, screw, tack, pin, or nail.

Example 24. The system of example 23 (as well as subject matter of one or more of any combination of examples 2-22, in whole or in part), wherein said screw comprises a compression screw, fixation screw, cancellous screw, cortical screw, or machine screw.

Example 25. The system of example 1 (as well as subject matter of one or more of any combination of examples 2-24, in whole or in part), wherein said aperture comprises at least one or more of any combination of the following: fenestration, slot, gap, slit, hole, and perforation.

Example 26. The system of example 1 (as well as subject matter of one or more of any combination of examples 2-25, in whole or in part), further comprising an imaging apparatus for imaging said system or portions of the system.

Example 27 The system of example 1 (as well as subject matter of one or more of any combination of examples 2-26, in whole or in part), wherein the biomaterial and/or biologically active agents comprises at least one or more of any combination of the following: bone substitute, bone cement, infection preventative agent, biologics, antibiotics, bone morphogenic proteins, hydrogels, hydrogel microspheres, scaffold, scaffold components, cytokines, and chemokines.

Example 28. The system of example 1 (as well as subject matter of one or more of any combination of examples 2-27, in whole or in part), further comprising a guide member provided together in a kit with said apparatus.

29. The system of example 1 (as well as subject matter of one or more of any combination of examples 2-28, in whole or in part), wherein said guide member is a guide wire, pin, or needle.

Example 30. A surgical kit comprising:
a guide member; and
a bone fixation system for promoting the union of a bone fracture and fusion of bones across a joint space at a target region of a subject, said system comprising:
- a surgical implant device, comprising a surgical implant device proximal end, a surgical implant device distal end and a surgical implant device longitudinal member there between and a surgical implant device bore running longitudinally there through, said surgical implant device bore comprising a surgical implant device bore proximal opening and a surgical implant device bore distal opening;
- a plurality of apertures disposed on said surgical implant device longitudinal member providing a fluidic passage between an outer surface of said surgical implant device longitudinal member and said surgical implant device bore;
- said surgical implant device bore proximal opening being configured to provide a fluidic passage for biomaterial material and/or biologically active agents therein;
- said surgical implant device bore being configured to be inserted over said guide member and a to have said guide member advanced or retracted therein; and
- said surgical implant device bore distal opening being configured to be sealed by said guide member while said guide member is partially absent from said surgical implant device bore thereby defining a guide member-absent bore area in said surgical implant device bore to allow the biomaterial and/or biologically active agents jo extrude or diffuse from at least one of said apertures located in the guide member-absent bore area to the target region of the subject.

Example 31. The kit of example 30 (as well as subject matter of one or more of any combination of examples 2-29, in whole or in part), further comprising:
- said surgical implant device bore distal opening being configured to provide a fluidic passage for biomaterial material and/or biologically active agents therein; and
- said surgical implant device bore proximal opening being configured to be sealed by said guide member while said guide member is partially absent from said surgical implant device bore thereby defining a guide member-absent bore area in said surgical implant device bore to allow the biomaterial and/or biologically active agents to extrude or diffuse from at least one of said apertures located in the guide member-absent bore area to the target region of the subject.

Example 32. A method for promoting the union of a bone fracture and/or fusion of bones across a joint space at a target region of a subject, said method comprising:
- inserting a surgical implant device at the target region, said surgical implant device comprising:
  - a surgical implant device proximal end, a surgical implant device distal end and a surgical implant device longitudinal member there between and a surgical implant device bore running longitudinally there through, said surgical implant device bore comprising a surgical implant device bore proximal opening and a surgical implant device bore distal opening;
  - a plurality of apertures disposed on said surgical implant device longitudinal member providing a fluidic passage between an outer surface of said surgical implant device longitudinal member and said surgical implant device bore; and
  - said surgical implant device bore opening being configured to provide a fluidic passage for biomaterial material and/or biologically active agents therein;
- providing a guide member in said surgical implant device bore;
- sealing said surgical implant device bore distal opening or said surgical implant device bore proximal opening with said guide member; and
- positioning said guide member relative to said surgical implant device to provide for said guide member to be partially absent from said surgical implant device bore thereby defining a guide member-absent bore area in said surgical implant device bore to allow the biomaterial and/or biologically active agents to extrude or diffuse from at least one of said apertures located in the guide member-absent bore area to the target region of the subject.

Example 33. The method of example 32, further comprising:
- attaching an interface device in fluidic communication with said surgical implant device proximal end, wherein said interface device is configured to provide a fluidic passage for the biomaterial and/or biologically active agents to travel through said interface device to said surgical implant device.

Example 34. The method of example 33, wherein said attaching of said interface device is implemented percutaneously.

Example 35. The method of example 33 (as well as subject matter in whole or in part of example 34), wherein said attaching of said interface device is implemented endoscopically.

Example 36. The method of example 33 (as well as subject matter of one or more of any combination of examples 34-35, in whole or in part), wherein said attaching of said interface device further comprises fixedly rotating said surgical implant device.

Example 37. The method of example 33 (as well as subject matter of one or more of any combination of examples 34-36, in whole or in part), wherein said attaching of said interface device further comprises frictionally fitting into said surgical implant device.

Example 38. The method of example 32 (as well as subject matter of one or more of any combination of examples 34-37, in whole or in part), further comprising:
- attaching an interface device in fluidic communication with said surgical implant device distal end, wherein said interface device is configured to provide a fluidic passage for the biomaterial to travel through said interface device to said surgical implant device.

Example 39. The method of example 38, wherein said attaching of said interface device is implemented percutaneously.

Example 40. The method of example 38 (as well as subject matter of one or more of any combination of example 39, in whole or in part), wherein said attaching of said interface device is implemented endoscopically.

Example 41. The method of example 38 (as well as subject matter of one or more of any combination of examples 39-40, in whole or in part), wherein said attaching of said interface device further comprises fixedly rotating said surgical implant device.

Example 42. The method of example 38 (as well as subject matter of one or more of any combination of examples 39-41, in whole or in part), wherein said attaching of said interface device further comprises frictionally fitting into said surgical implant device.

Example 43. The method of example 38 (as well as subject matter of one or more of any combination of examples 39-42, in whole or in part), further comprising: fixedly rotating said surgical implant device at said surgical implant device distal end.

Example 44. The method of example 38 (as well as subject matter of one or more of any combination of examples 39-43, in whole or in part), further comprising:

attaching a biomaterial and/or biologically active agents delivery device in fluidic communication with said interface device.

Example 45. The method of using any of the systems (devices, structures, apparatuses, or material) or their components or sub-components provided in any one or more of examples 1-31, in whole or in part.

Example 46. The method of manufacturing any of the systems (devices, structures, apparatuses, or material) or their components or sub-components provided in any one or more of examples 1-31, in whole or in part.

Example 47. A non-transitory machine readable medium including instructions for promoting the union of a bone fracture and/or fusion of bones across a joint space at a target region of a subject, which when executed by a machine, cause the machine to perform any of the steps or activities provided in any one or more of examples 32-44.

Example 48. A non-transitory computer readable medium including program instructions for promoting the union of a bone fracture and/or fusion of bones across a joint space at a target region of a subject, wherein execution of the program instructions by one or more processors of a computer system causes the processor to carry out: any of the steps or activities provided in any one or more of examples 32-44.

Example 50. Writing instructions for promoting the union of a bone fracture and/or fusion of bones across a joint space at a target region of a subject, which when executed by a user, causes the user to perform any of the steps or activities provided in any one or more of examples 32-44.

Example 51. The system of example 1, further comprising: said surgical implant device bore proximal opening being configured to allow said guide member to be removed from said surgical implant device bore through said surgical implant device bore proximal opening.

Example 52. The system of example 51, further comprising:

said surgical implant device bore distal opening being configured to allow said guide member to be removed from said surgical implant device bore through said surgical implant device bore distal opening.

REFERENCES

The devices, systems, apparatuses, imaging techniques, compositions, materials, machine readable medium, computer program products, biomaterial, biologically active agents, screws, implant threading and apertures, guide wires, medical devices, medical procedures, fittings, connections/connectors, and methods of various embodiments of the invention disclosed herein may utilize aspects (e.g., devices, systems, apparatuses, imaging techniques, compositions, materials, machine readable medium, computer program products, biomaterial, biologically active agents, screws, implant threading and apertures, guide wires, medical devices, medical procedures, fittings, connections/connectors, and methods) disclosed in the following references, applications, publications and patents and which are hereby incorporated by reference herein in their entirety, and which are not admitted to be prior art with respect to the present invention by inclusion in this section:

1. Wolf J M, Dawson L, Mountcastle, S B, Owens B D, "The incidence of scaphoid fracture in a military population", Injury, 2009; 40(12):1316-1319. doi:10.1016/j.injury.2009.03.045.
2. Papp S., "Carpal Bone Fractures", Hand Clin. 2010; 26(1):119-127. doi:10.1016/j.hcl.2009.08.014.
3. Adams J E, Steinmann S P, "Acute Scaphoid Fractures", Hand Clin. 2010; 26(1):97-103. doi:10.1016/j.hcl.2009.08.007.
4. Brogan D M, Moran S L, Shin A Y, "Outcomes of open reduction and internal fixation of acute proximal pole scaphoid fractures", Hand (N Y). 2015; 10(2):227-232, doi:10.1007/s11552-014-9689-8.
5. Elhassan B T, Shin A Y, "Scaphoid Fracture in Children", Hand Clin. 2006; 22(1):31-41. doi:10.1016/j.hcl.2005.10.004.
6. Nih L R, Sideris E, Carmichael S T, Segura T., "Injection of Microporous Annealing Particle (MAP) Hydrogels in the Stroke Cavity Reduces Gliosis and Inflammation and Promotes NPC Migration to the Lesion", Adv Mater. 2017; 29(32):1606471. doi:10.1002/adma.201606471.
7. Doornberg J N, Buijze G A, Ham S J, Ring D, Bhandari M, Poolman R W, "Nonoperative Treatment for Acute Scaphoid Fractures: A Systematic Review and Meta-Analysis of Randomized Controlled Trials", J Trauma Inj Infect Crit Care. 2011; 71(4):1073-1081. doi:10.1097/TA.0b013e318222f485.
8. Giddins G., "The Nonoperative Management of Hand Fractures in United Kingdom", Hand Clin. 2017; 33(3): 473-487. doi:10.1016/j.hcl.2017.04.006.
9. Compson J P, Heatley F W, "Imaging the position of a screw within the scaphoid. A clinical, anatomical and radiological study", J Hand Surg Br. 1993; 18(6):716-724. http://www.ncbi.nlm.nih.gov/pubmed/8308428. Accessed Oct. 29, 2017.
10. Buijze G A, Ochtman L, Ring D., "Management of Scaphoid Nonunion", J Hand Surg Am. 2012; 37(5):1095-1100. doi:10.1016/j.jhsa.2012.03.002.
11. Rizzo M, Shin A Y, "Treatment of acute scaphoid fractures in the athlete", Curr Sports Med Rep. 2006; 5(5):242-248. http://www.ncbi.nlm.nih.gov/pubmed/16934205. Accessed Jul. 15, 2017.
12. Bond C D, Shin C A, "Percutaneous cannulated screw fixation of acute scaphoid fractures", Tech Hand Up Extrem Surg. 2000; 4(2):81-87. http://www.ncbi.nlm.nih.gov/pubmed/16609395. Accessed Jul. 15, 2017.
13. Streli R., "[Percutaneous screwing of the navicular bone of the hand with a compression drill screw (a new method)], Zentralbl Chir. 1970; 95(36):1060-1078. http://www.ncbi.nlm.nih.gov/pubmed/5474468. Accessed Jul. 15, 2017.
14. Davis E N, Chung K C, Kotsis S V, Lau F H, Vijan S., "A Cost/Utility Analysis of Open Reduction and Internal Fixation versus Cast Immobilization for Acute Nondisplaced Mid-Waist Scaphoid Fractures", Plast Reconstr Surg. 2006; 117(4):1223-1235. doi:10.1097/01.prs.0000201461.71055.83.
15. Nwachukwu B U, Schairer W W, O'Dea E, McCormick F, Lane J M, "The Quality of Cost-Utility Analyses in Orthopedic Trauma", Orthopedics. 2015; 38(8):e673-e680. doi:10.3928/01477447-20150804-53.
16. Munk B, Larsen C F. "Bone grafting the scaphoid nonunion A systematic review of 147 publications including 5 246 cases of scaphoid nonunion. Acta Orthop Scand. 2004; 75(5):618-629. doi: 10.1080/00016470410001529.
17. Merrell G A, Wolfe S W, Slade J F, "Treatment of scaphoid nonunions: quantitative meta-analysis of the literature", J Hand Surg Am. 2002; 27(4):685-691. http://www.ncbi.nlm.nih.gov/pubmed/12132096. Accessed Nov. 28, 2017.
18. Pinder R M, Brkljac M, Rix L, Muir L, Brewster M, "Treatment of Scaphoid Nonunion: A Systematic Review of the Existing Evidence", J Hand Surg Am. 2015; 40(9): 1797-1805.e3. doi:10.1016/j.jhsa.2015.05.003.
19. Shah C M, Stern P J, "Scapholunate advanced collapse (SLAC) and scaphoid nonunion advanced collapse (SNAC) wrist arthritis", Curr Rev Musculoskelet Med. 2013; 6(1):9-17. doi:10.1007/s12178-012-9149-4.
20. Tobin E J., "Recent coating developments for combination devices in orthopedic and dental applications: A literature review", Adv Drug Deliv Rev. 2017; 112:88-100. doi:10.1016/j.addr.2017.01.007.
21. Pichler W, Windisch G, Schaffler G, Heidari N, Don K, Grechenig W., "Computer-Assisted 3-Dimensional Anthropometry of the Scaphoid. Orthopedics", 2010; 33(2):85-88. doi:10.3928/01477447-20100104-16.
22. Gibbs D M R, Black C R M, Dawson J I, Oreffo R O C, "A review of hydrogel use in fracture healing and bone regeneration", J Tissue Eng Regen Med. 2016; 10(3):187-198. doi:10.1002/term.1968.
23. Sideris E, Griffin D R, Ding Y, et al., "Particle Hydrogels Based on Hyaluronic Acid Building Blocks", ACS Biomater Sci Eng. 2016; 2(11):2034-2041. doi:10.1021/acsbiomaterials.6b00444.
24. Griffin D R, Weaver W M, Scumpia P O, Di Carlo D, Segura T., "Accelerated wound healing by injectable microporous gel scaffolds assembled from annealed building blocks", Nat Mater. 2015; 14(7):737-744. doi: 10.1038/nmat4294.
25. Hak D J, Makino T, Niikura T, Hazelwood S J, Curtiss S, Reddi A H, "Recombinant human BMP-7 effectively prevents non-union in both young and old rats", J Orthop Res. 2006; 24(1):11-20. doi:10.1002/jor.20022.
26. Garcia P, Histing T, Holstein J H, et al., "Rodent animal models of delayed bone healing and non-union formation: a comprehensive review", Eur Cell Mater. 2013; 26:1-12-4. http://www.ncbi.nlm.nih.gov/pubmed/23857280. Accessed Oct. 29, 2017.
27. Beutel B G, Melamed E, Hinds R M, Gottschalk M B, Capo J T, "Mechanical Evaluation of Four Internal Fixation Constructs for Scaphoid Fractures", Hand (N Y). 2016; 11(1):72-77. doi:10.1177/1558944715614889.
28. McCallister W V, Knight J, Kaliappan R, Trumble T E, "Central placement of the screw in simulated fractures of the scaphoid waist: a biomechanical study", J Bone Joint Surg Am. 2003; 85-A(1):72-77. http://www.ncbi.nlm.nih.gov/pubmed/12533575. Accessed Oct. 30, 2017.
29. Tholpady S S, DeGeorge B R, Campbell C A, "The Effect of Local Rho-Kinase Inhibition on Murine Wound Healing", Ann Plast Surg. 2014; 72(6):5213-5219. doi: 10.1097/SAP.0000000000000150.
30. DeGeorge B R, Ning B, Salopek L S, et al., "Advanced Imaging Techniques for Investigation of Acellular Dermal Matrix Biointegration", Plast Reconstr Surg. 2017; 139(2):395-405. doi:10.1097/PRS.0000000000002992.
31. DeGeorge B R, Holland M C, Drake D B, "The impact of conflict of interest in abdominal wall reconstruction with acellular dermal matrix", Ann Plast Surg. 2015; 74(2):242-247. doi:10.1097/SAP.0000000000000372.
32. DeGeorge B R, Rodeheaver G T, Drake D B, "The Biophysical Characteristics of Human Composite Flexor Tendon Allograft for Upper Extremity Reconstruction", Ann Plast Surg. 2014; 72 (6):S184-S190. doi:10.1097/SAP.0000000000000097.
33. Fowler J R, Hughes T B, 'Scaphoid Fractures', Clin Sports Med. 2015; 34(1):37-50. doi:10.1016/j.csm.2014.09.011.
34. Zamanian, Kamran and Freeze D., "US Orthopedic Trauma Device Market To Exceed 8 Billion By 2020", https://www.meddeviceonline.com/doc/u-s-orthopedic-trauma-device-market-to-exceed-eight-billion-dollars-0001. Accessed Nov. 22, 2017.
35. U.S. Pat. No. 9,265,540 B2, Kirschman, "Minimally Invasive Spinal Facet Compression Screw and System for Bone Joint Fusion and Fixation", Feb. 23, 2016.
36. U.S. Patent Application Publication No. US 2007/0233123 A1, Ahmad, et al., "Bone Fixation Device", Oct. 4, 2007.
37. U.S. Pat. No. 8,216,243 B2, Yevmenenko, et al., "Headless Compression Screw with Integrated Reduction—Compression Instrument", Jul. 10, 2012.
38. U.S. Pat. No. 8,979,911 B2, Martineau, et al., "Porous Bone Screw", Mar. 17, 2015.
39. International Patent Appl. Publ. No. WO 02/098307 A1 (PCT/AU02/00482), Little, D., (The Royal Alexandria Hospital for Children), "A Device for the Delivery of a Drug to a Fractured Bone", Dec. 12, 2002.
40. AU02/00482, The Royal Alexandria Hospital for Children", A Device for the Delivery of a Drug to a Fractured Bone, May 7, 2002 (2001 Priority Document for PCT/AU02/00482, Little, D., 5/7/02.
41. Arcam A B. (n.d.). "Arcam-Ti6A14V-Titanium-Alloy". http://www.arcam.com/wp-content/uploads/Arcam-Ti6A14V-Titanium-Alloy.pdf.
42. Fowler, J. R., & Hughes, T. B. (2015), "Scaphoid fractures", Clinics in Sports Medicine, 34(1), 37-50. https://doi.org/10.1016/j.csm.2014.09.011.
43. Kawamura, K., & Chung, K. C. (2008), "Treatment of Scaphoid Fractures and Nonunions", The Journal of Hand Surgery, 33(6), 988-997. https://doi.org/10.1016/j.jhsa.2008.04.026.
44. Pensy, R. A., Richards, A. M., Belkoff, S. M., Mentzer, K., & Andrew Eglseder, W. (2009), "Biomechanical comparison of two headless compression screws for scaphoid fixation", Journal of Surgical Orthopaedic Advances, 18(4), 182-188.
45. Renkin, E. M. (1954), "Filtration, diffusion, and molecular sieving through porous cellulose membranes", The Journal of General Physiology, 38(2), 225-243.
46. Schafer, D. (n.d.), "Strength Requirements and Characteristics of Pipe and Well Screen for Deep Water Well Applications, 17.
47. Schuind, F., Cooney, W. P., Linscheid, R. L., An, K. N., & Chao, E. Y. S. (1995), "Force and pressure transmission through the normal wrist. A theoretical two-dimensional study in the posteroanterior plane", Journal of Biomechanics, 28(5), 587-601. https://doi.org/10.1016/0021-9290(94)00093-J.
48. Sendher, R., & Ladd, A. L. (2013), "The Scaphoid", Orthopedic Clinics of North America, 44(1), 107-120. https://doi.org/10.1016/j.ocl.2012.09.003.
49. Steinmann, S. P., & Adams, J. E. (2006), "Scaphoid fractures and nonunions: diagnosis and treatment," Journal of Orthopaedic Science, 11(4), 424-431. https://doi.org/10.1007/s00776-006-1025-x.

50. Swedish Standards Institution. (1997, February 28), "Conical fittings with a 6% (Luer) taper for syringes, needles, and certain other medical equipment—Lock fittings", Retrieved Feb. 16, 2019, from https://www.sis.se/api/document/preview/20126/.
51. Ten Berg, P., Drijkoningen, T., Strackee, S., & Buijze, G. (2016), "Classifications of Acute Scaphoid Fractures: A Systematic Literature Review", Journal of Wrist Surgery, 05(02), 152-159. https://doi.org/10.1055/s-0036-1571280.
52. Zura, R., Xiong, Z., Einhorn, T., Watson, J. T., Ostrum, R. F., Prayson, M. J., Steen, R. G. (2016), "Epidemiology of Fracture Nonunion in 18 Human Bones", JAMA Surgery, 151(11), e162775. https://doi.org/10.1001/jamasurg.2016.2775.
53. Boyd, et al., "Splints and Casts: Indications and Methods", American Family Physician, www.aafp.org/afp, Vol. 80, No. 5, Sep. 1, 2009, pages 492-499
54. TriMed Inc.— "Home/Cannulated Screw System/1.7, 2.3, 3.0 & 3.5 mm Screws", https://trimedortho.com/portfolio-items/1-7-2-3-3-0-3-5 mm-screws, pages 1-4.

Unless clearly specified to the contrary, there is no requirement for any particular described or illustrated activity or element, any particular sequence or such activities, any particular size, speed, material, duration, contour, dimension or frequency, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A bone fixation system for promoting the union of a bone fracture and fusion of bones across a joint space at a target region of a subject, said system comprising:
   a surgical implant device, comprising a surgical implant device proximal end, a surgical implant device distal end and a surgical implant device longitudinal member there between and a surgical implant device bore running longitudinally there through said surgical implant device longitudinal member along its longitudinal axis, said surgical implant device bore comprising a surgical implant device bore proximal opening on said longitudinal axis and a surgical implant device bore distal opening on said longitudinal axis;
   a plurality of apertures disposed on said surgical implant device longitudinal member providing a fluidic passage between an outer surface of said surgical implant device longitudinal member and said surgical implant device bore;
   said surgical implant device bore proximal opening being configured to provide a fluidic passage for biomaterial material and/or biologically active agents therein;
   said surgical implant device bore, said surgical implant device bore distal opening, and said surgical implant device bore proximal opening being configured to be inserted over a guide member and a to have the guide member advanced or retracted therein said surgical device bore;
   said surgical implant device bore distal opening being configured to be sealed by the guide member disposed in said surgical implant device bore distal opening while said guide member is partially absent from said surgical implant device bore thereby defining a guide member-absent bore area in said surgical implant device bore to allow the biomaterial and/or biologically active agents to extrude or diffuse from at least one of said apertures located in the guide member-absent bore area to the target region of the subject;
   a surgical implant device attachment and sealant mechanism disposed on said surgical implant device proximal end;
   wherein said surgical implant device attachment and sealant mechanism, said surgical implant device bore, and said plurality of apertures are configured to provide a fluidic passage for biomaterial material and/or biologically active agents to travel through said surgical implant device attachment and sealant mechanism, said surgical implant device bore, and said plurality of apertures to allow the biomaterial and/or biologically active agents to extrude or diffuse from at least one of said apertures to the target region of the subject; and
said surgical implant device bore distal opening is configured as a male to female type fitting.

2. The system of claim 1, further comprising:
said surgical implant device bore distal opening being configured to allow said guide member to be removed from said surgical implant device bore through said surgical implant device bore distal opening.

3. The system of claim 1, wherein said surgical implant device proximal end is configured to be accessed percutaneously.

4. The system of claim 1, wherein said surgical implant device proximal end is configured to be accessed endoscopically.

5. The system of claim 1, wherein said surgical implant device distal end is configured to be accessed percutaneously.

6. The system of claim 1, wherein said surgical implant device distal end is configured to be accessed endoscopically.

7. The system of claim 1, further comprising:
an interface device, comprising an interface device proximal end, an interface device distal end and an interface device longitudinal member there between and an interface device bore running longitudinally there through;
an interface device proximal attachment and sealant mechanism disposed on said interface device said proximal end;
an interface device distal attachment and sealant mechanism disposed on said interface device said distal end;
said interface device distal attachment and sealant mechanism configured to fasten to said surgical implant device attachment and sealant mechanism to provide a fixed and fluidic type sealed connection thereto; and
wherein said interface device proximal attachment and sealant mechanism, said interface device bore, said interface device distal attachment and sealant mechanism are configured to provide a fluidic passage for the biomaterial and/or biologically active agents to travel through said interface device proximal attachment and sealant mechanism, said interface device bore, said interface device distal attachment and sealant mechanism to said surgical implant device attachment and sealant mechanism.

8. The system of claim 7, further comprising:
a biomaterial and/or biologically active agents delivery device, comprising biomaterial and/or biologically active agents delivery device proximal end, a biomaterial and/or biologically active agents delivery device distal end and a biomaterial and/or biologically active agents delivery device longitudinal member there between and a biomaterial and/or biologically active agents delivery device bore running longitudinally there through;
a biomaterial delivery and/or biologically active agents distal device attachment and sealant mechanism disposed on said biomaterial and/or biologically active agents delivery device distal end;
said biomaterial and/or biologically active agents delivery distal attachment and sealant mechanism configured to fasten to said interface device proximal attachment and sealant mechanism to provide a fixed and fluid type sealed connection thereto; and
wherein said biomaterial and/or biologically active agents delivery device bore and said biomaterial and/or biologically active agents delivery device distal attachment and sealant mechanism are configured to provide a fluidic passage for the biomaterial and/or biologically active agents to travel through said biomaterial and/or biologically active agents delivery device bore and said biomaterial and/or biologically active agents delivery device distal attachment and sealant mechanism to said interface device attachment and sealant mechanism.

9. The system of claim 7, further comprising:
a biomaterial and/or biologically active agents delivery device, comprising a biomaterial and/or biologically active agents delivery device proximal end, a biomaterial and/or biologically active agents delivery device distal end and a biomaterial and/or biologically active agents delivery device longitudinal member there between and a biomaterial and/or biologically active agents delivery device bore running longitudinally there through; and
wherein said biomaterial and/or biologically active agents delivery device is configured to provide a fluidic passage for the biomaterial and/or biologically active agents to travel through said biomaterial and/or biologically active agents delivery device to said interface device.

10. The system of claim 1, further comprising:
an interface device, comprising an interface device proximal end, an interface device distal end and an interface device longitudinal member there between and an interface device bore running longitudinally there through; and
wherein said interface device is configured to provide a fluidic passage for the biomaterial and/or biologically active agents to travel through said interface device to said surgical implant device.

11. The system of claim 1, wherein:
said surgical implant device attachment and sealant mechanism is a male to female type fitting.

12. The system of claim 11, wherein:
said interface device distal attachment and sealant mechanism is a male to female type fitting.

13. The system of claim 12, wherein:
said interface device proximal attachment and sealant mechanism is a male to female type fitting.

14. The system of claim 13, wherein:
said biomaterial and/or biologically active agents delivery distal attachment and sealant mechanism is male to female fitting.

15. The system of claim 12, wherein:
said interface device distal attachment and sealant mechanism is a Luer Lock fitting.

16. The system of claim 15, wherein:
said biomaterial and/or biologically active agents delivery distal attachment and sealant mechanism is a Luer Lock fitting.

17. The system of claim 1, further comprising:
a distal section of threads disposed at said surgical implant device distal end.

18. The system of claim 17, further comprising:
a proximal section of threads disposed at said surgical implant device proximal end.

19. The system of claim 1, further comprising:
a proximal section of threads disposed at said surgical implant device proximal end.

20. The system of claim 1, wherein said surgical implant device comprises a dowel, screw, tack, pin, or nail.

21. The system of claim 20, wherein said screw comprises a compression screw, fixation screw, cancellous screw, cortical screw, or machine screw.

22. The system of claim 1, wherein said aperture comprises at least one or more of any combination of the following: fenestration, slot, gap, slit, hole, and perforation.

23. The system of claim 1, further comprising an imaging apparatus for imaging said system or portions of the system.

24. The system of claim 1, wherein the biomaterial and/or biologically active agents comprises at least one or more of any combination of the following: bone substitute, bone cement, infection preventative agent, biologics, antibiotics, bone morphogenic proteins, hydrogels, hydrogel microspheres, scaffold, scaffold components, cytokines, and chemokines.

25. The system of claim 1, further comprising a guide member provided together in a kit with said apparatus.

26. The system of claim 1, wherein said guide member is a guide wire, pin, or needle.

27. The system of claim 1, further comprising:
   said surgical implant device bore proximal opening being configured to allow said guide member to be removed from said surgical implant device bore through said surgical implant device bore proximal opening.

28. The system of claim 27, further comprising:
   said surgical implant device bore distal opening being configured to allow said guide member to be removed from said surgical implant device bore through said surgical implant device bore distal opening.

* * * * *